United States Patent
Cole et al.

(10) Patent No.: US 10,987,467 B2
(45) Date of Patent: Apr. 27, 2021

(54) CANNULA DEPLOYMENT MECHANISM

(71) Applicant: Becton, Dickinson and Company, Franklin Lakes, NJ (US)

(72) Inventors: Russell Cole, River Vale, NJ (US); Alyssa Jackson, Philadelphia, PA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 32 days.

(21) Appl. No.: 16/229,166

(22) Filed: Dec. 21, 2018

(65) Prior Publication Data

US 2019/0117885 A1 Apr. 25, 2019

Related U.S. Application Data

(62) Division of application No. 14/261,386, filed on Apr. 24, 2014, now Pat. No. 10,195,342.

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 2005/14252* (2013.01); *A61M 2005/1585* (2013.01)

(58) Field of Classification Search
CPC .......... A61M 5/158; A61M 2005/1581; A61M 5/14248; A61M 2005/14252; A61M 2005/1585
See application file for complete search history.

(56) References Cited

U.S. PATENT DOCUMENTS

| | | | |
|---|---|---|---|
| 6,740,059 B2 | 5/2004 | Flaherty | |
| 6,830,562 B2 | 12/2004 | Mogensen et al. | |
| 6,960,192 B1 | 11/2005 | Flaherty et al. | |
| 6,997,907 B2 | 2/2006 | Safabash et al. | |
| 7,207,974 B2 | 4/2007 | Safabash et al. | |
| 7,771,412 B2 | 8/2010 | Anderson et al. | |
| 7,909,791 B2 | 3/2011 | Liniger et al. | |
| 8,152,771 B2 | 4/2012 | Mogensen et al. | |
| 8,167,841 B2 | 5/2012 | Teissen-Simony et al. | |
| 8,475,410 B2 | 7/2013 | Kaufmann et al. | |

(Continued)

FOREIGN PATENT DOCUMENTS

| | | |
|---|---|---|
| JP | 2004-521667 A | 7/2004 |
| JP | 2010-531197 A | 9/2010 |

(Continued)

*Primary Examiner* — Nathan R Price
*Assistant Examiner* — Melissa A Snyder
(74) *Attorney, Agent, or Firm* — Dickinson Wright PLLC

(57) ABSTRACT

A cannula insertion device is disclosed. The device includes a needle carriage, a rail device on which the needle carriage is slidable, a yoke having a channel, a linkage connected to the needle carriage and extending into the channel, a torsion spring with one end connected to the linkage, and locking device for locking the torsion spring in tension and maintaining the needle carriage and the linkage in a locked position prior to activation. Upon release of the locking device, the tension of the torsion spring is released, which causes the linkage to move in the channel and slide the needle carriage along the rail device. A catheter carriage may also be provided for actuation by the linkage.

8 Claims, 22 Drawing Sheets

(56) References Cited

U.S. PATENT DOCUMENTS

| | | |
|---|---|---|
| 2005/0065466 A1* | 3/2005 | Vedrine ............ A61M 5/14248 604/93.01 |
| 2008/0319414 A1 | 12/2008 | Yodfat et al. |
| 2009/0192471 A1 | 7/2009 | Carter et al. |
| 2010/0152674 A1* | 6/2010 | Kavazov ............... A61M 5/165 604/218 |
| 2011/0054285 A1* | 3/2011 | Searle ............... A61M 5/14244 600/365 |
| 2012/0209190 A1 | 8/2012 | Gray et al. |
| 2013/0018317 A1 | 1/2013 | Bobroff et al. |
| 2013/0138078 A1 | 5/2013 | Smith et al. |
| 2013/0204191 A1 | 8/2013 | Cindrich et al. |
| 2013/0253472 A1 | 9/2013 | Cabiri |
| 2014/0058353 A1 | 2/2014 | Politis et al. |
| 2014/0088509 A1 | 3/2014 | Sonderegger et al. |

FOREIGN PATENT DOCUMENTS

| | | |
|---|---|---|
| WO | WO-0220073 A2 | 3/2002 |
| WO | WO-2004006982 A2 | 1/2004 |
| WO | WO-2014049886 A1 | 8/2016 |

* cited by examiner

CANNULA DEPLOYMENT MECHANISM

CROSS REFERENCE TO RELATED APPLICATION

This application is a division of U.S. patent application Ser. No. 14/261,386, filed Apr. 24, 2014, the disclosure of which is incorporated herein by reference in its entirety.

FIELD OF THE INVENTION

The present invention relates generally to a cannula deployment mechanism. More particularly, the present invention relates to a catheter deployment mechanism for an insulin patch pump.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

There are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

There are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Unlike a conventional infusion pump and infusion set combination, a patch pump is an integrated device that combines most or all of the fluidic components, including the fluid reservoir, a pumping mechanism and a mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted.

As a patch pump is designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced in size as much as possible. One such part is the insertion mechanism for automatically inserting the cannula into the user's skin.

In order to minimize the height of the cannula insertion mechanism, some conventional insertion mechanisms are configured to insert the cannula at an acute angle from the surface of the skin, e.g. 30-45 degrees. However, it may be preferable to insert the cannula perpendicular or close to perpendicular to the surface of the skin, since this requires the minimum length of cannula insertion. With the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump, itself.

Accordingly, a need exists for an improved insertion cannula mechanism for use in a limited space environment, such as in a patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

An object of the present invention is to substantially address the above and other concerns and provide a cannula deployment mechanism that is suitable for use in a confined or limited space, such as in an insulin patch pump.

Another object of the present invention is to provide an insertion device for inserting a cannula, in the form of an introducer needle and catheter, into an infusion site and retracting only the introducer needle while the catheter remains attached at the infusion site.

Another object of the present invention is to provide an insertion device with a reduced height for incorporation into a patch pump having a reduced overall height.

Another object of the present invention is to provide an inserter device that can insert an introducer needle and catheter into a user's skin substantially perpendicular to the surface of the user's skin.

Another object of the present invention is to provide an insertion device that requires relatively few components but is effective in inserting and retracting the introducer needle.

Another object of the present invention is to provide an insertion device that is cost-effective and reliable.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

Figure 1:
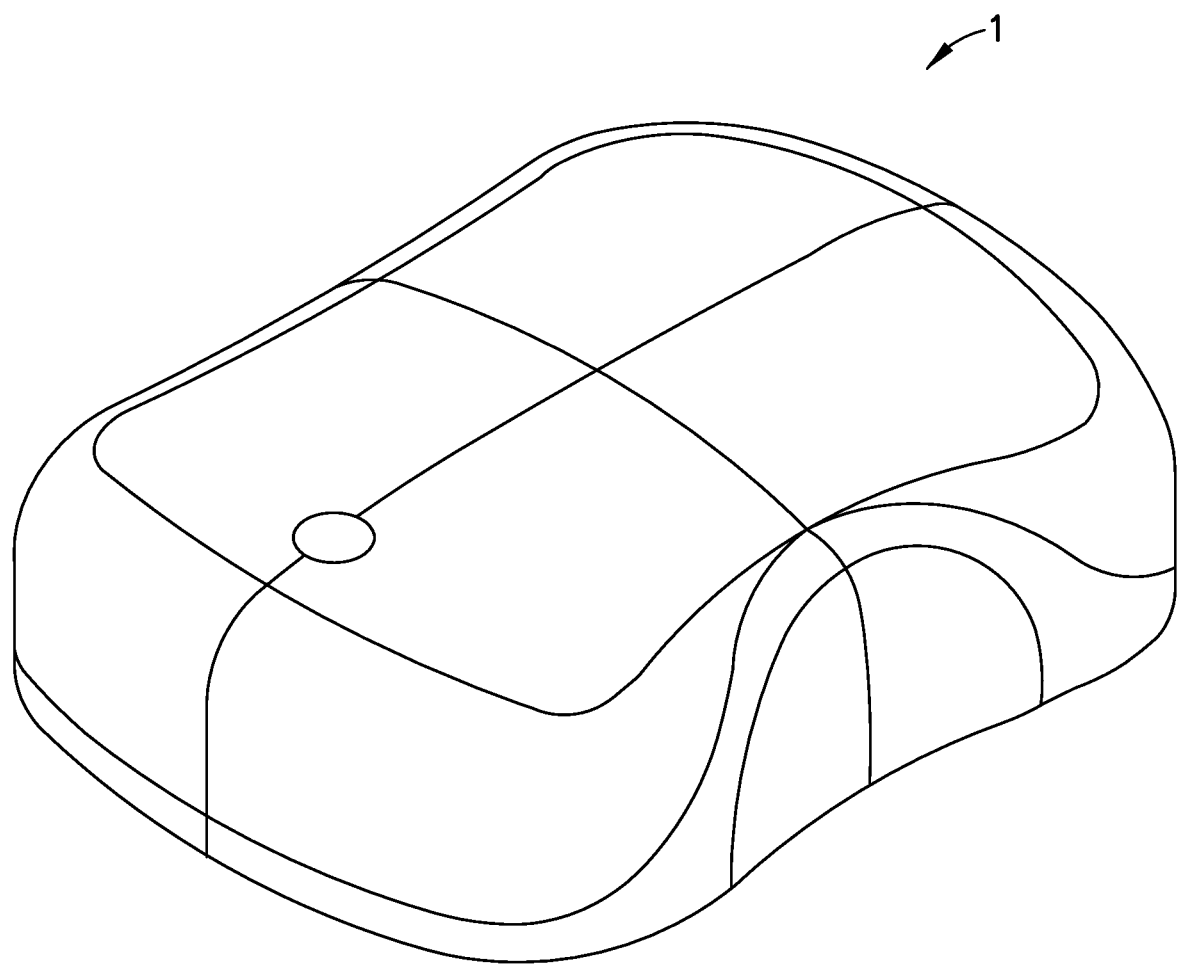
FIG. 1 is a perspective view of a patch pump incorporating a low-profile cannula insertion device.
Figure 2:
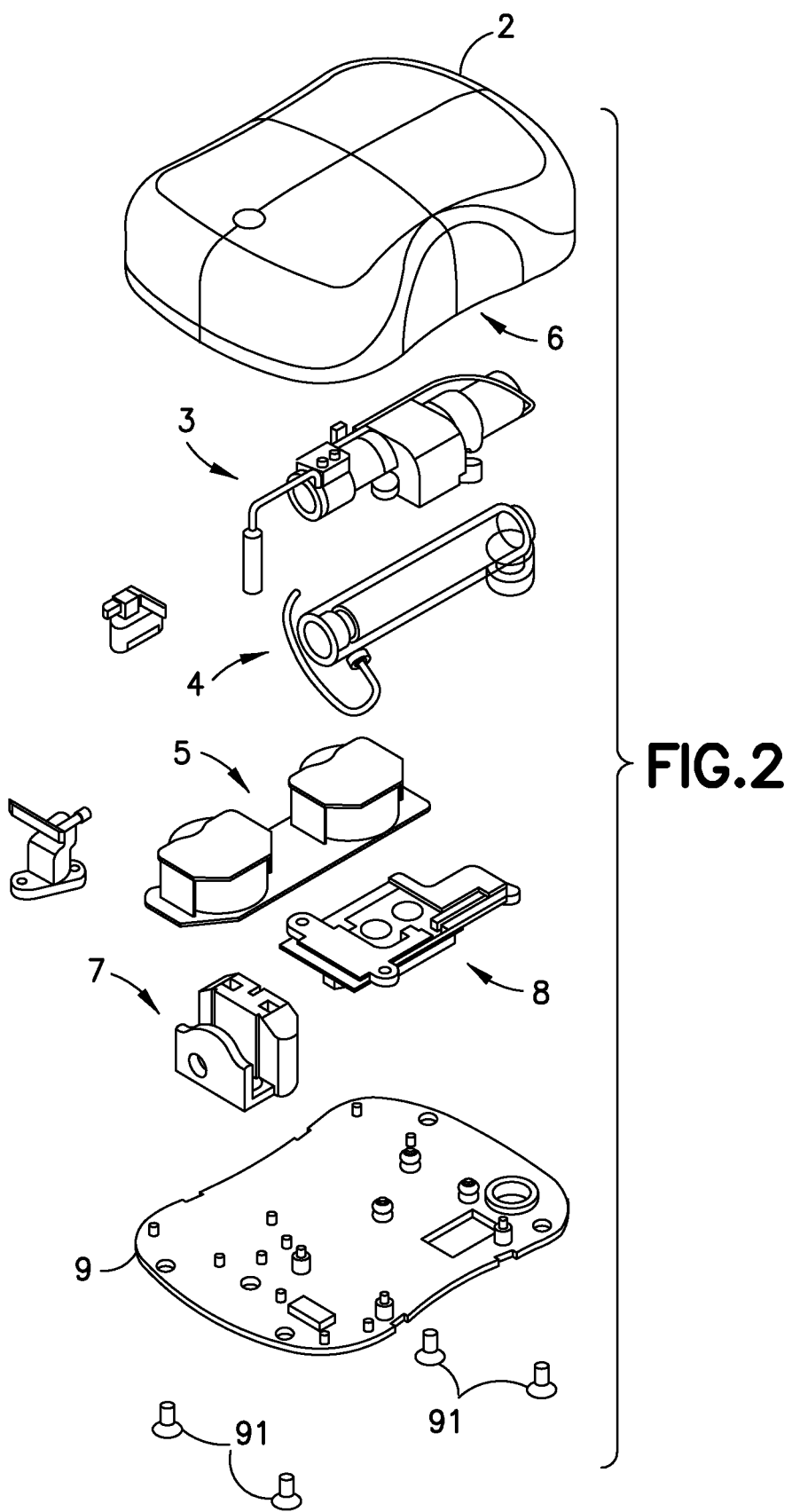
FIG. 2 is an exploded view of the various components of the patch pump of FIG. 1.

FIG. 1 is an external perspective view of an exemplary embodiment of a patch pump 1. FIG. 2 is an exploded view of the various components of the patch pump 1 of FIG. 1. The components of the patch pump 1 may include a reservoir 4 for storing insulin; a pump 3 for pumping insulin out of the reservoir 4; a power source 5 in the form of one or more batteries; an insertion mechanism 7 for inserting an introducer needle with a catheter into a user's skin; control electronics 8 in the form of a circuit board with optional communications capabilities to outside devices such as a remote controller, computer, or a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

Figure 3:
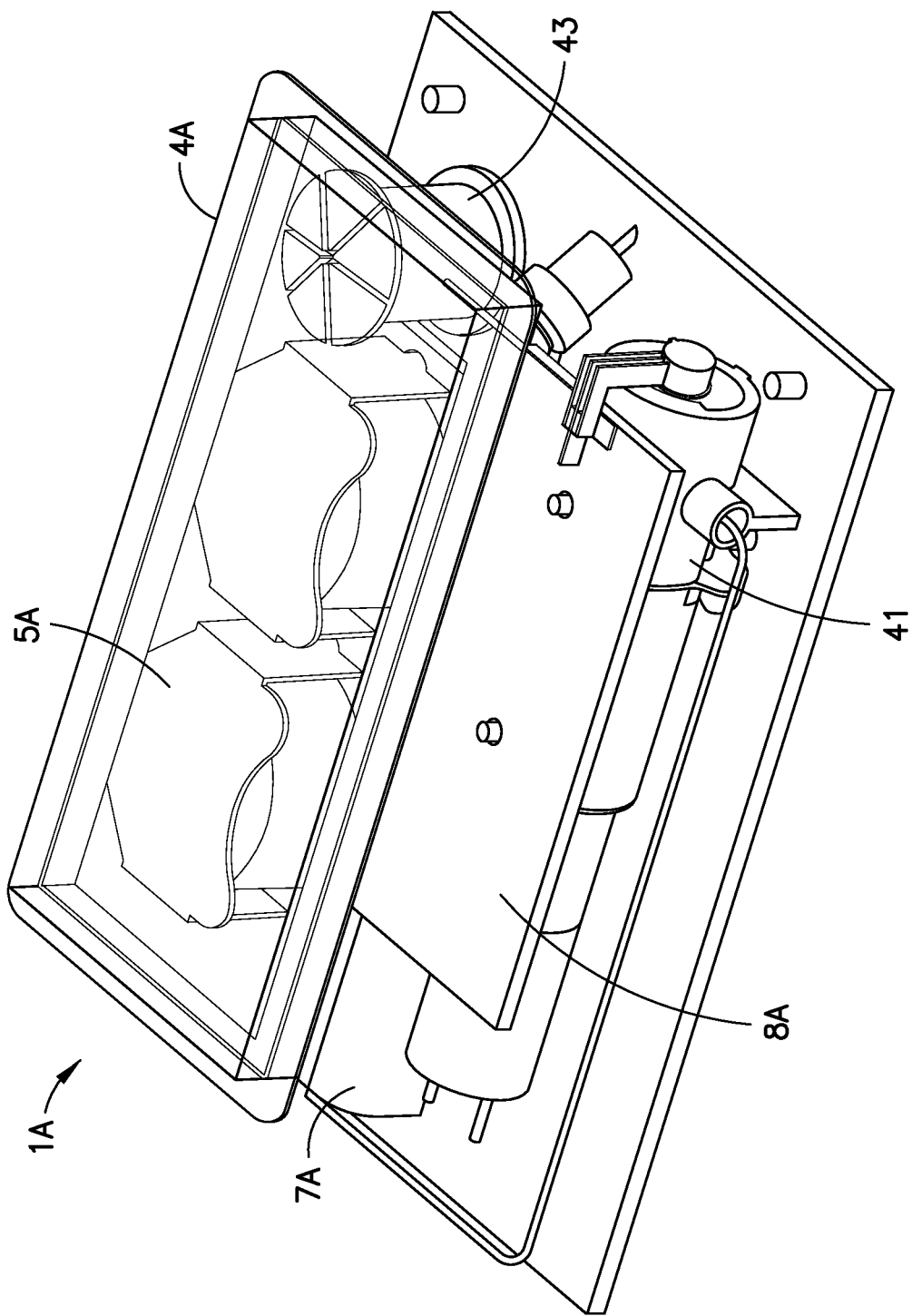
FIG. 3 is a perspective view of an alternative design for a patch pump having a flexible reservoir, illustrated without a cover.

FIG. 3 is a perspective view of an alternative design for a patch pump 1A having a flexible reservoir 4A, and is illustrated without a cover. Such arrangement may further reduce the external dimensions of the patch pump 1A, with the flexible reservoir 4A filling voids within the patch pump 1A. The patch pump 1A is illustrated with a cannula insertion device 7A that inserts the cannula, typically at an acute angle, less than 90 degrees, into the surface of a user's skin. The patch pump 1A further comprises a power source 5A in the form of batteries; a metering sub-system 41 that monitors the volume of insulin and includes a low volume detecting ability; control electronics 8A for controlling the components of the device; and a reservoir fill port 43 for receiving a fill syringe 45 to fill the reservoir 4A.

Figure 4:
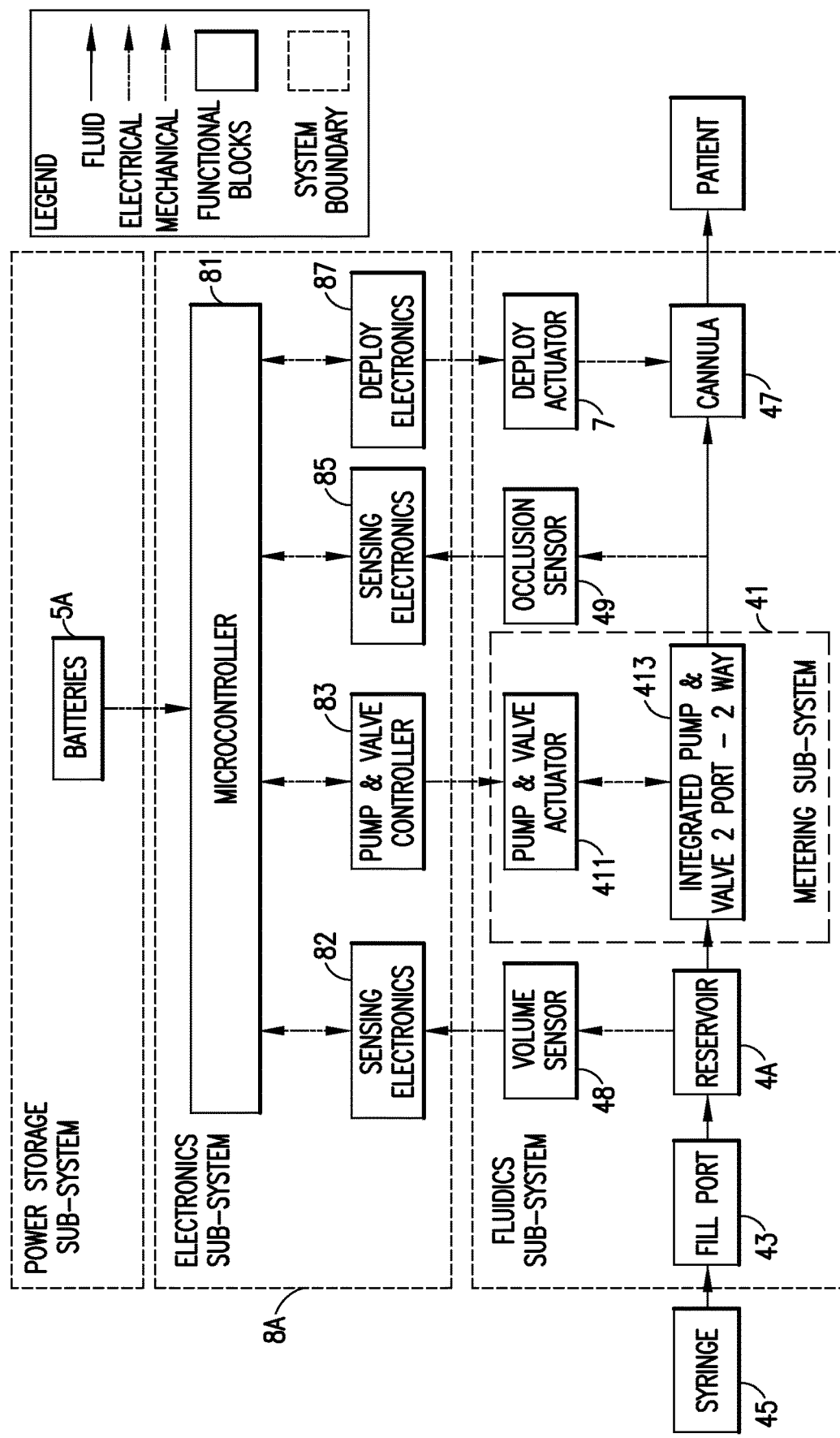
FIG. 4 is a fluidic architecture and metering sub-system diagram of the patch pump of FIG. 3.

FIG. 4 is a fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85 and deployment electronics 87, that control the operation of the patch pump 1A. The patch pump 1A includes a fluidics sub-system that comprises a reservoir 4A, a volume sensor 48 for the reservoir 4A, and a reservoir fill port 43 for receiving a fill syringe 45 to fill the reservoir 4A. The fluidics sub-system may include a metering system comprising a pump and valve actuator 411 and an integrated pump and valve mechanism 413. The fluidics sub-system may further include an occlusion sensor 49, a deploy actuator or cannula insertion device 7, as well as the cannula 47 for insertion into an infusion site on the user's skin. The architecture for the patch pump 1 of FIGS. 1 and 2 can be the same or similar to that which is illustrated in FIG. 4.

Figure 5:
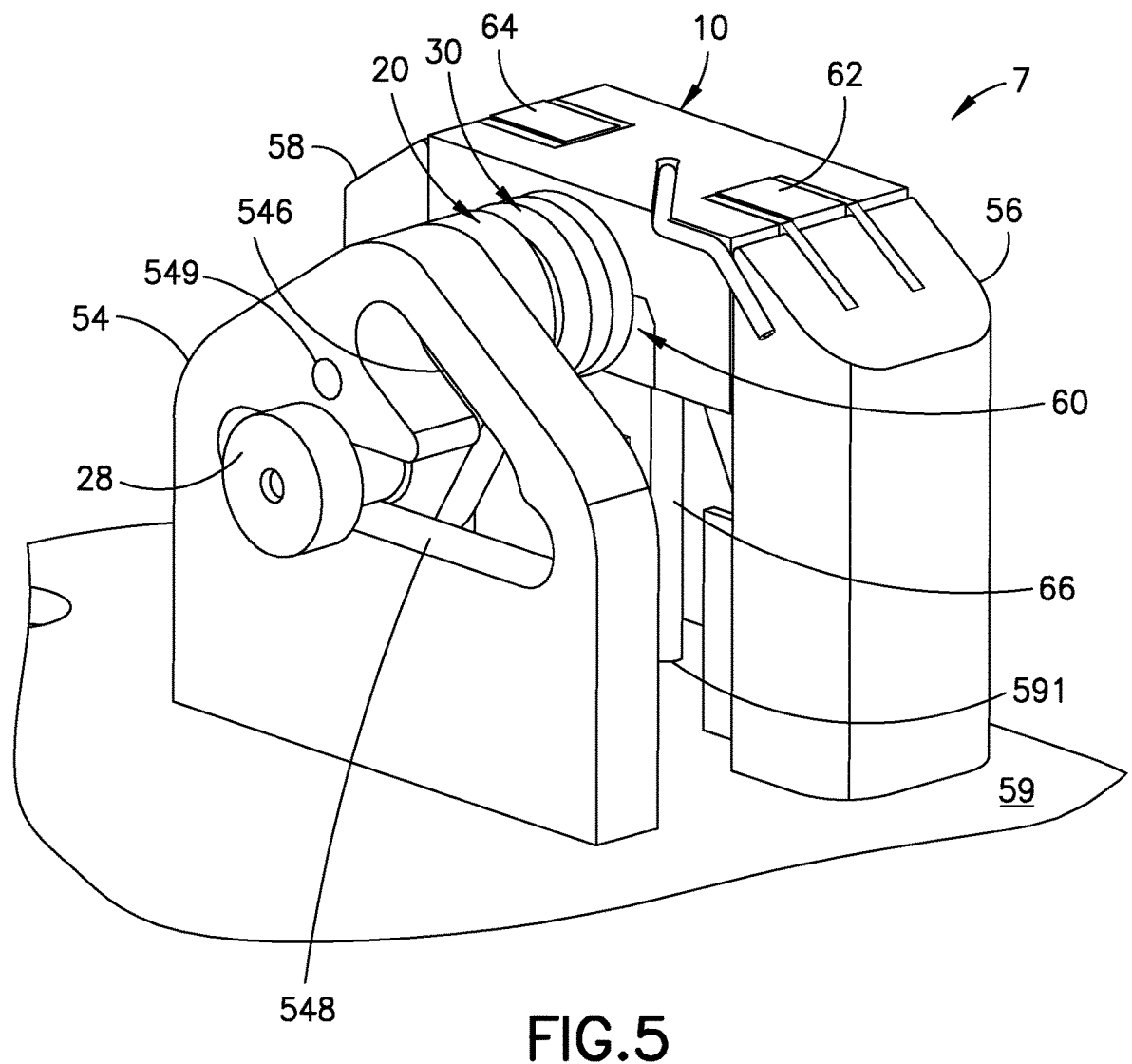
FIG. 5 is a perspective view of a cannula insertion device.

FIG. 5 is a perspective view of an exemplary embodiment of the cannula insertion device 7, which can be used as the cannula insertion device for the patch pump 1 and 1A. The purpose of the cannula insertion device 7 is to insert a catheter 66 into the skin of a user. A hollow introducer needle 70 (illustrated in FIG. 6) attached to a needle carriage 10 is slid into the catheter 66 which is attached to a catheter carriage 60. FIG. 5 illustrates the device with the metal torsion spring 30 that has been tensioned around a linkage 20 and locked in place by a pin 90 (illustrated in FIGS. 19-21). Upon removal of the pin 90, the tension in the tensioned torsion spring 30 is released to cause the cannula insertion device 7 to be actuated to the insert the introducer needle 70 and the catheter 66 into a user's skin or infusion site and to retract only the introducer needle 70 from the user's skin, such that only the catheter 66 remains in the user's skin.

The catheter deployment mechanism or cannula insertion device 7 is configured for use in an insulin patch pump, but it is conceivable that the design or variations thereof can be used for any similar purpose in which a needle is inserted and retracted, with or without a catheter. Upon activation, the cannula insertion device 7 inserts a soft plastic catheter 66 and an introducer needle 70 perpendicularly or substantially perpendicularly to the surface of a user's skin to a preferred depth of about 5.3 mm, and automatically retracts the introducer needle 70, by using an adaptation of a Scotch yoke. A button press (not shown) on the patch pump 1 or 1A or an internal electrical actuator (not shown) can initiate the cannula insertion by removing the pin 90. The button on the patch pump 1 or 1A can operate mechanically or electrically. A remote control device (not shown) can also actuate the cannula insertion device 7.

The metal torsion spring 30 that powers the Scotch yoke is loaded or rotatively tensioned in the pre-activation state. The torsion spring 30 is mounted on the axle post 12 (see FIG. 6) of the needle carriage 10. A linkage 20 connects the needle carriage 10 to a yoke 54. When the torsion spring 30 is released, the linkage 20 and yoke 54 converts the rotational motion (approximately 300 degrees) of the metal spring 30 into a vertical descending motion of the needle carriage 10 which in turn pushes on the catheter carriage 60 to push the introducer needle 70 and the catheter 66 into the skin of the user, followed by a vertical ascending of only the needle carriage 10 which withdraws the introducer needle 70 without retracting the catheter 66 from the user's skin.

The relatively large spring rotation angle (approximately 300 degrees) allows for a smaller linkage 20, which can reduce the overall height of the cannula insertion device 7 that is needed to achieve the required travel distance for the needle carriage 10. Such height reduction can permit a patch pump profile to be as low as 12.3 mm. The manner in which this is accomplished will be described in detail below.

Figure 6:
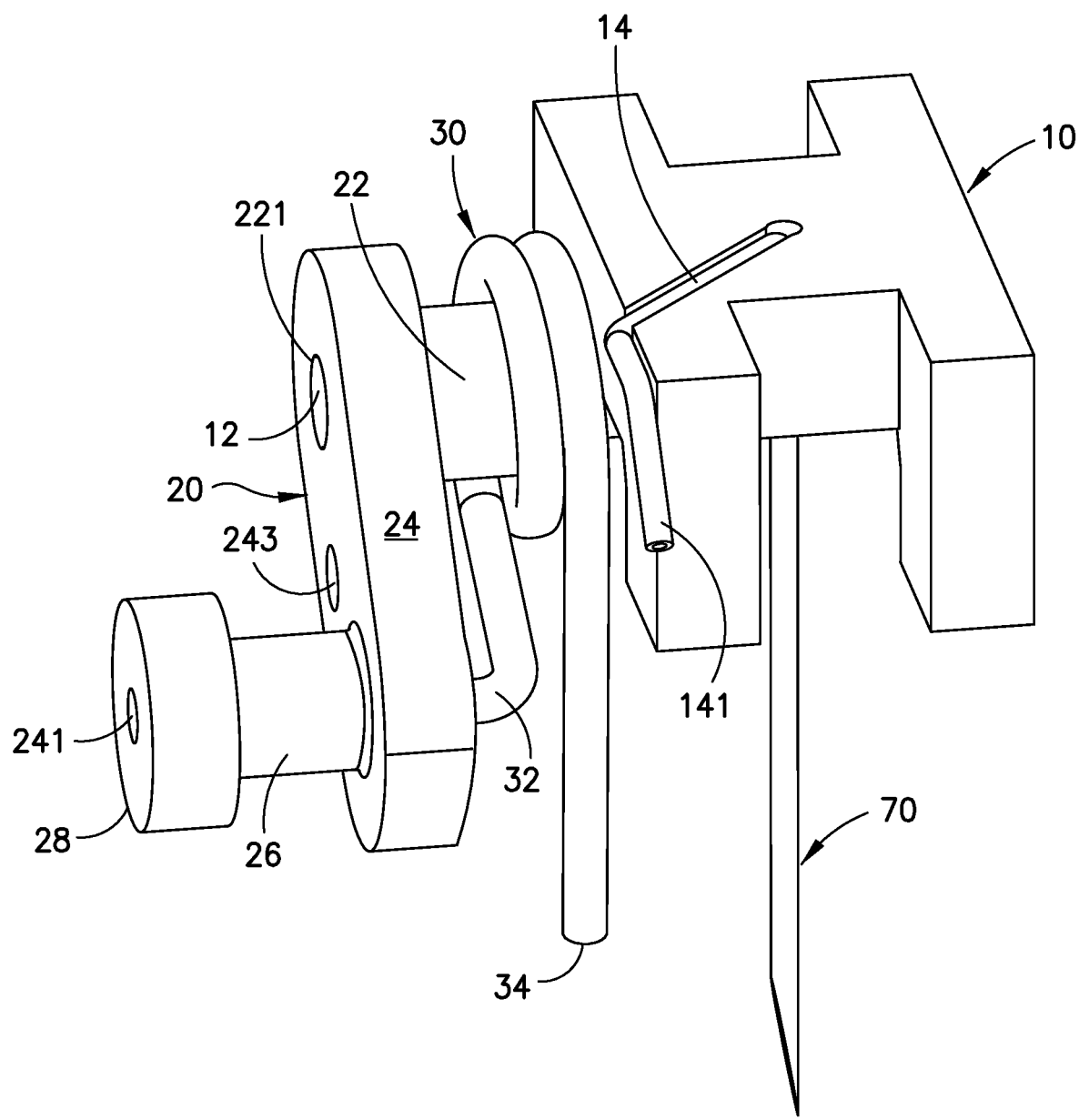
FIG. 6 is a perspective view of some of the components of the cannula insertion device of FIG. 5.
Figure 15:
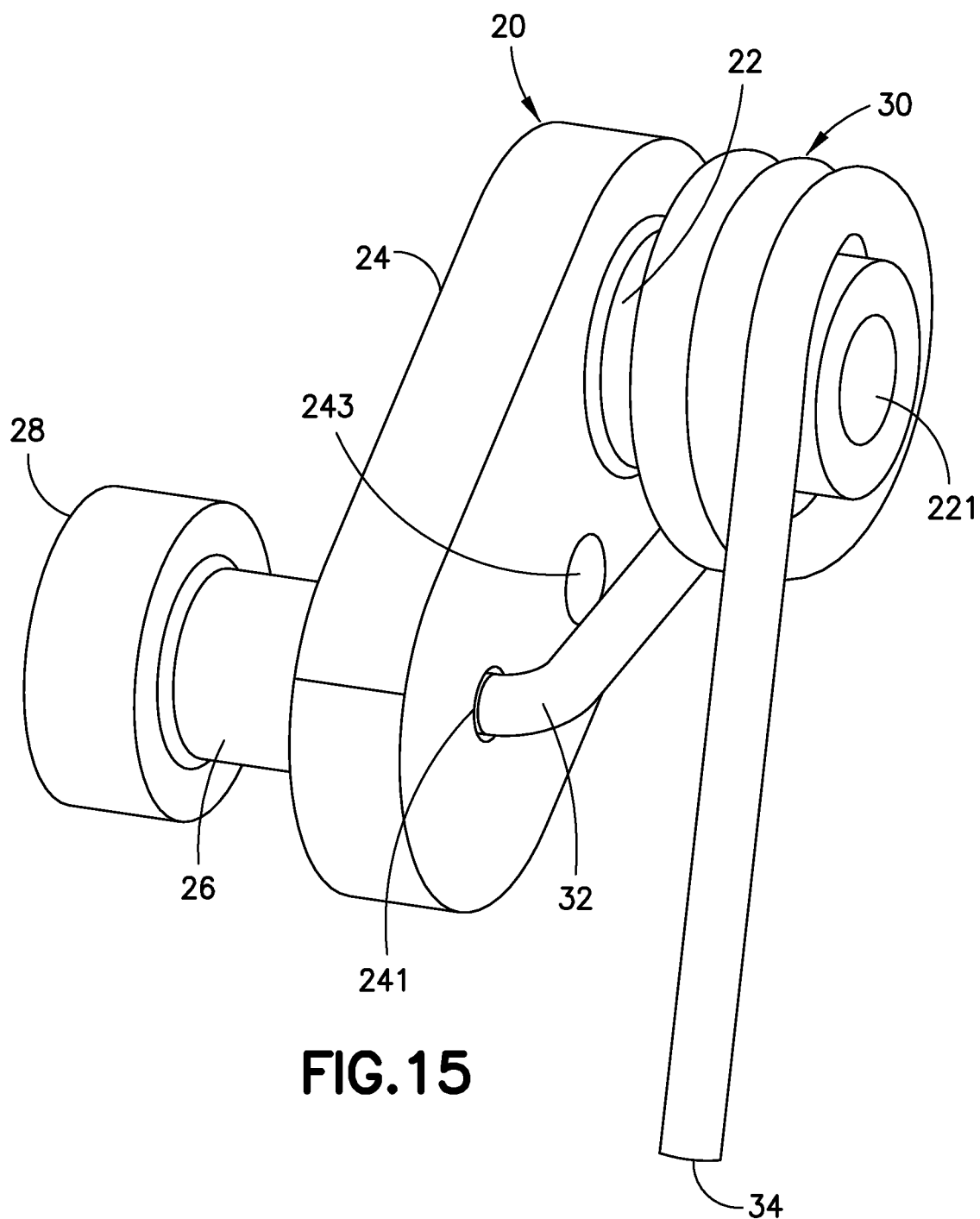
FIG. 15 is a perspective view of the linkage and the torsion spring of the inserter device of FIG. 5.

FIG. 6 is a perspective view of a subassembly of the cannula insertion device 7 of FIG. 5. The needle carriage 10 includes a cylindrical axle post 12 that is affixed to and extends outwardly from its main body. The linkage 20 includes a main flanged portion 24. Toward one end of the main flanged portion 24 extends a first post 22 with a hole 221 for rotatively receiving the axle post 12 of the needle carriage 10. The hole 221 may extend through the main flange portion 24, as illustrated in FIG. 6. Toward another end of the main flanged portion 24 extends, away from the first post 22, a second post 26. A mandrel 28 extends from the second post 26. The torsion spring 30 is positioned around the first post 22 of the linkage 20, and comprises a straight leg 34 and a bent leg 32. The bent leg 32 is attached to the main flanged portion 24 by being inserted into a hole 241 that may extend through the second post 26 and mandrel 28 (as illustrated in FIG. 15).

Figure 7:
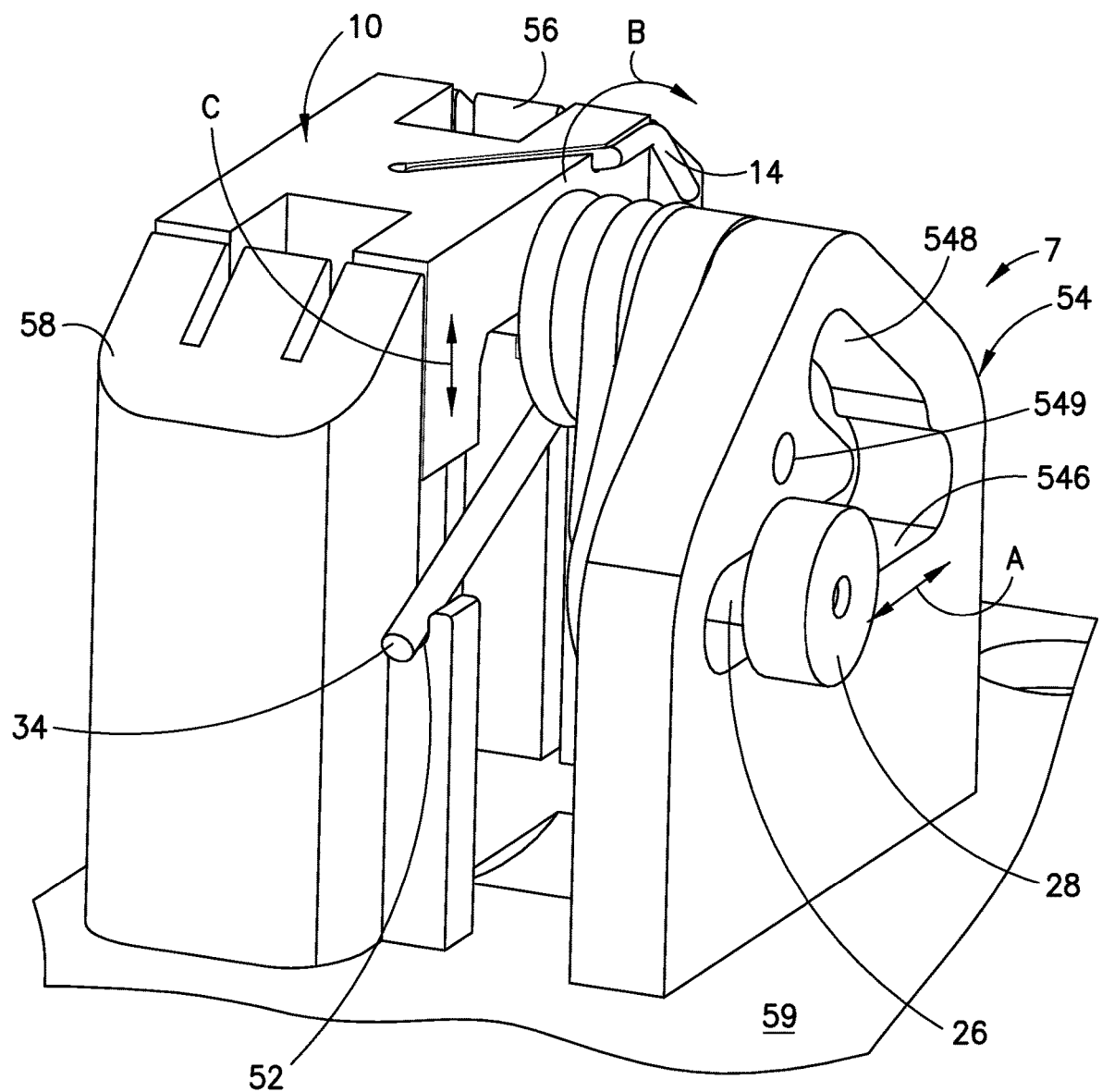
FIG. 7 is a perspective view of the insertion device of FIG. 5, illustrated with the needle carriage in an uppermost position, the open end of the torsion spring abutting a notch, and a portion of the linkage positioned in a channel of the yoke.

FIG. 7 is a perspective view of the cannula insertion device 7 of FIG. 5, illustrated with components of FIG. 6 shown in relation with a base floor 59 on which first and second base uprights 56, 58 and the yoke 54 are attached. The needle carriage 10 is illustrated at its uppermost position between the uprights 56, 58 and the straight leg 34 of the tensioned torsion spring 30 that has been wound around the first post 22 of the linkage 20, is abutted to or secured against a notch 52, illustrated in this embodiment as being part of the second base upright 58, and the second post 26 of the linkage 20 is positioned in a first channel 546 of the yoke 54. The pin 90 acts as locking mechanism that prevents the release of tension by the metal torsion spring 30, such that when the pin 90 is removed, tension on the torsion spring 30 is released which initiates the movements of the cannula insertion device 7. When the tension on the tension spring 30 is released, the first post 22 of linkage 20 rotates around the axle post 12 of the needle carriage 10 and the second post 26 of the linkage 20 slides left and right in the first channel 546 of the yoke 54, according to direction "A", and the rotation of the linkage 20 in direction "B", clockwise as is illustrated in FIG. 7, results in a vertical oscillation of the needle carriage 10 according to direction "C". Such movements of the cannula insertion device 7 will further be controlled by other components of the cannula insertion device 7, as described below.

Figure 8:
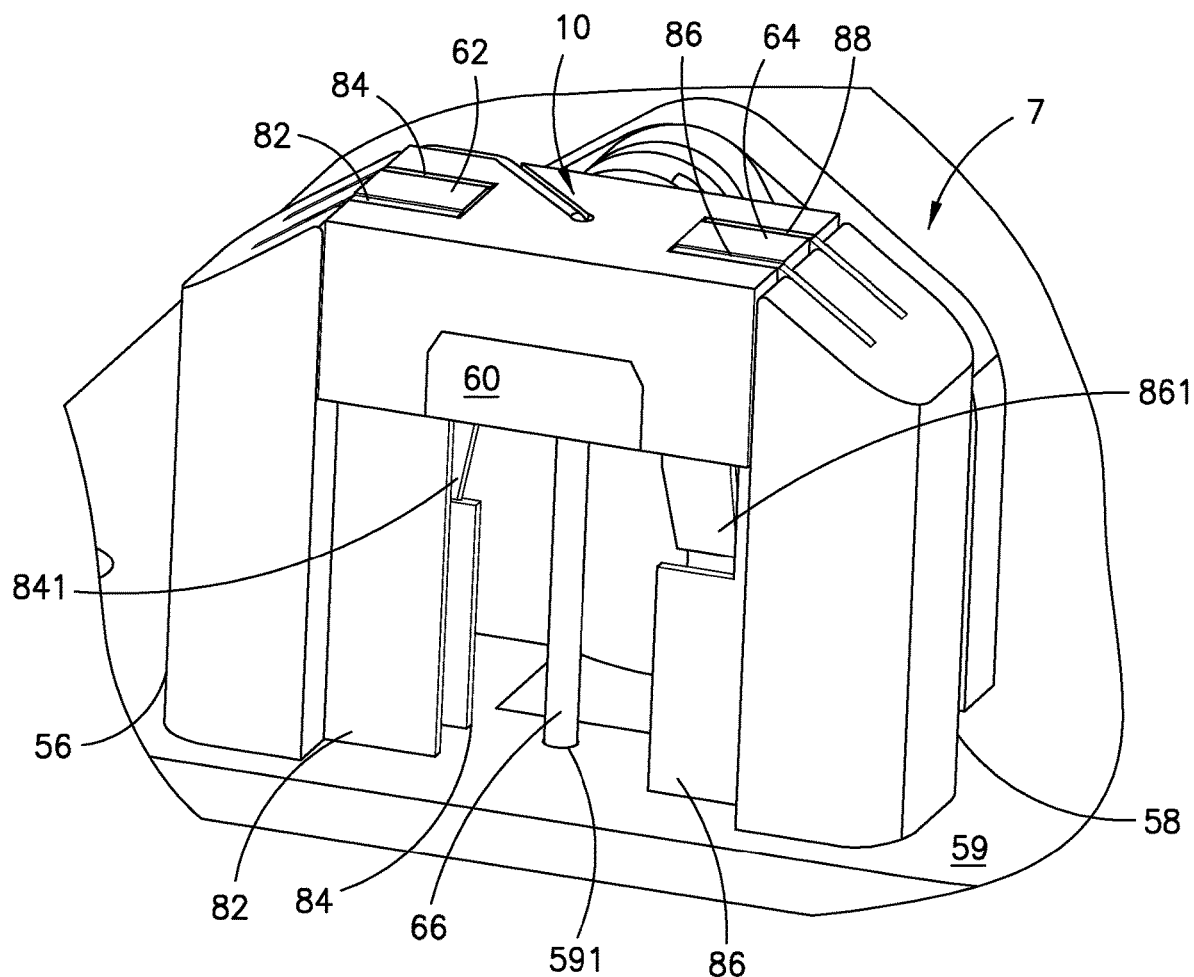
FIG. 8 is a perspective view of the insertion device of FIG. 5, illustrated with the needle carriage and the catheter carriage in an uppermost position, prior to the torsion spring being released.

FIG. 8 is a perspective view of the cannula insertion device 7 of FIG. 5, illustrated from an opposing view of FIG. 5, with the needle carriage 10 and the catheter carriage 60 in their uppermost positions (while being positioned between the rails 82, 84, 86, 88), prior to the torsion spring 30 being released. The base uprights 56, 58 include metal rails 82, 84, 86, 88 for the needle carriage 10 and catheter carriage 60 to slide on. The catheter carriage 60 includes a main body with a pair of slides 62, 64 that slide on the rails of the base uprights 56, 58, as illustrated in FIG. 8. Rails 84 and 86 include resilient metal tabs 841 and 861, respectively, and the tabs 841 and 861 pivot slightly inwardly toward opposing rails, 82 and 88 respectively. In other words, the tabs 841, 861 are bent into the slide track of the catheter carriage 60 formed by the rails 82, 84, 86, 88. The tabs 841 and 861 will restrict the sliding movement of the catheter carriage 60, as described below.

Figure 9:
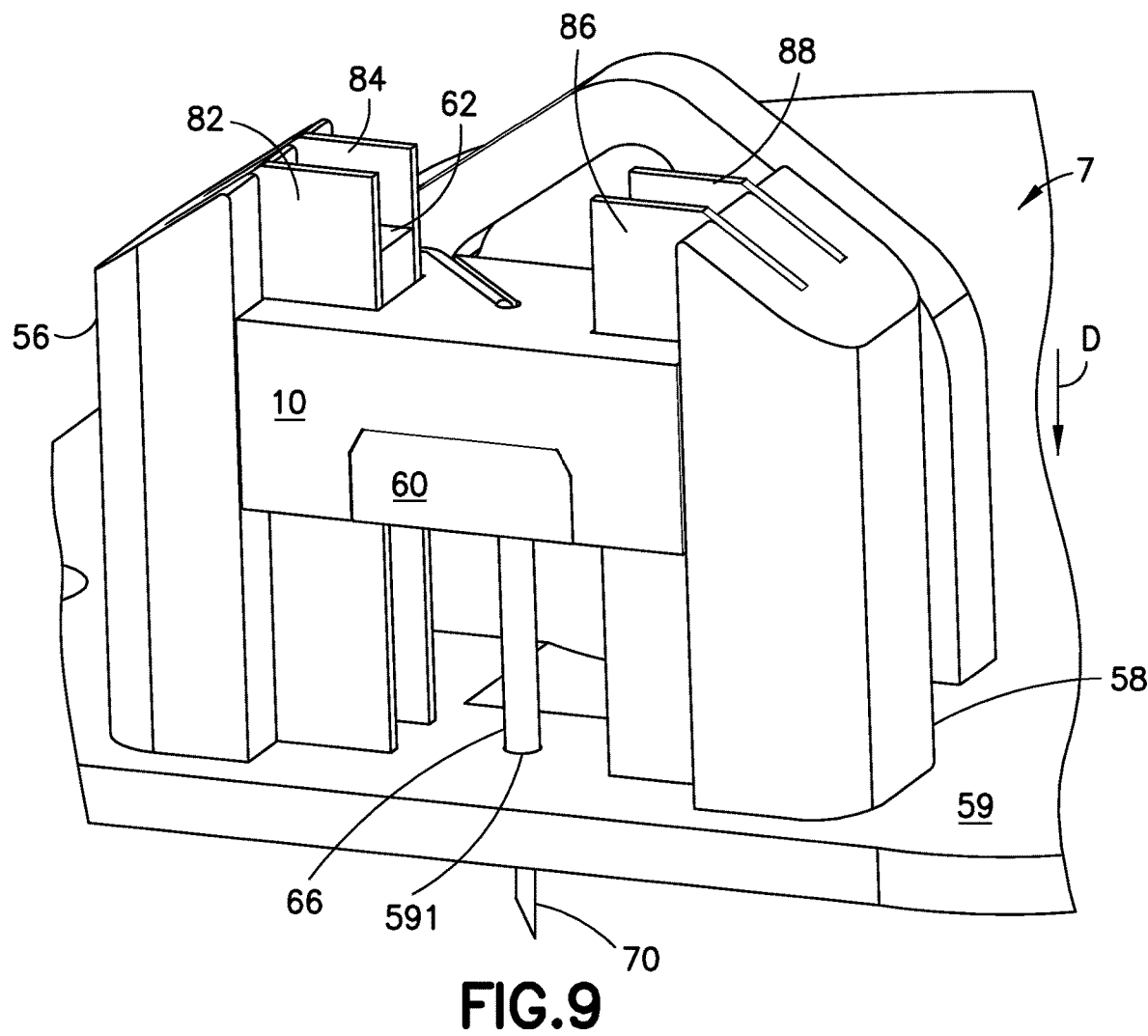
FIG. 9 is a perspective view of the insertion device of FIG. 8, illustrated with the needle carriage travelling downwardly with the catheter carriage, after the tension in the torsion spring is released.

FIG. 9 is a perspective view of the cannula insertion device 7 of FIG. 8, illustrated with the needle carriage 10 travelling downward together with the catheter carriage 60, the needle carriage 10 and catheter carriage 60 being nested together as illustrated, shortly after the torsion spring 30 has been released. As the needle carriage 10 travels downwardly in the carriage slide track formed by the rails 82, 84, 86, 88, according to direction "D", the needle carriage 10 slides past the slides 62, 64 of the catheter carriage 60 and presses on the catheter carriage 60, and both the needle carriage 10 and catheter carriage ride in rails 82, 84, 86, 88 in the first and second uprights 56, 58. The motion transferred to the needle carriage 10 from the spring 30 and linkage 20 slides the needle carriage 10 downwards along direction "D", and as the needle carriage 10 slides downward, it pushes the catheter carriage 60 downwardly as well.

The components of the cannula insertion device 7 can be made of various suitable materials, including plastics, metals and polymers that are well-known in the art. For instance, the rails 82, 84, 86, 88 is preferably metal as noted, but they can alternatively be made of Teflon® coated plastic or metal to reduce frictional resistance against the needle carriage 10 and the catheter carriage 60 sliding thereon.

Figure 10:
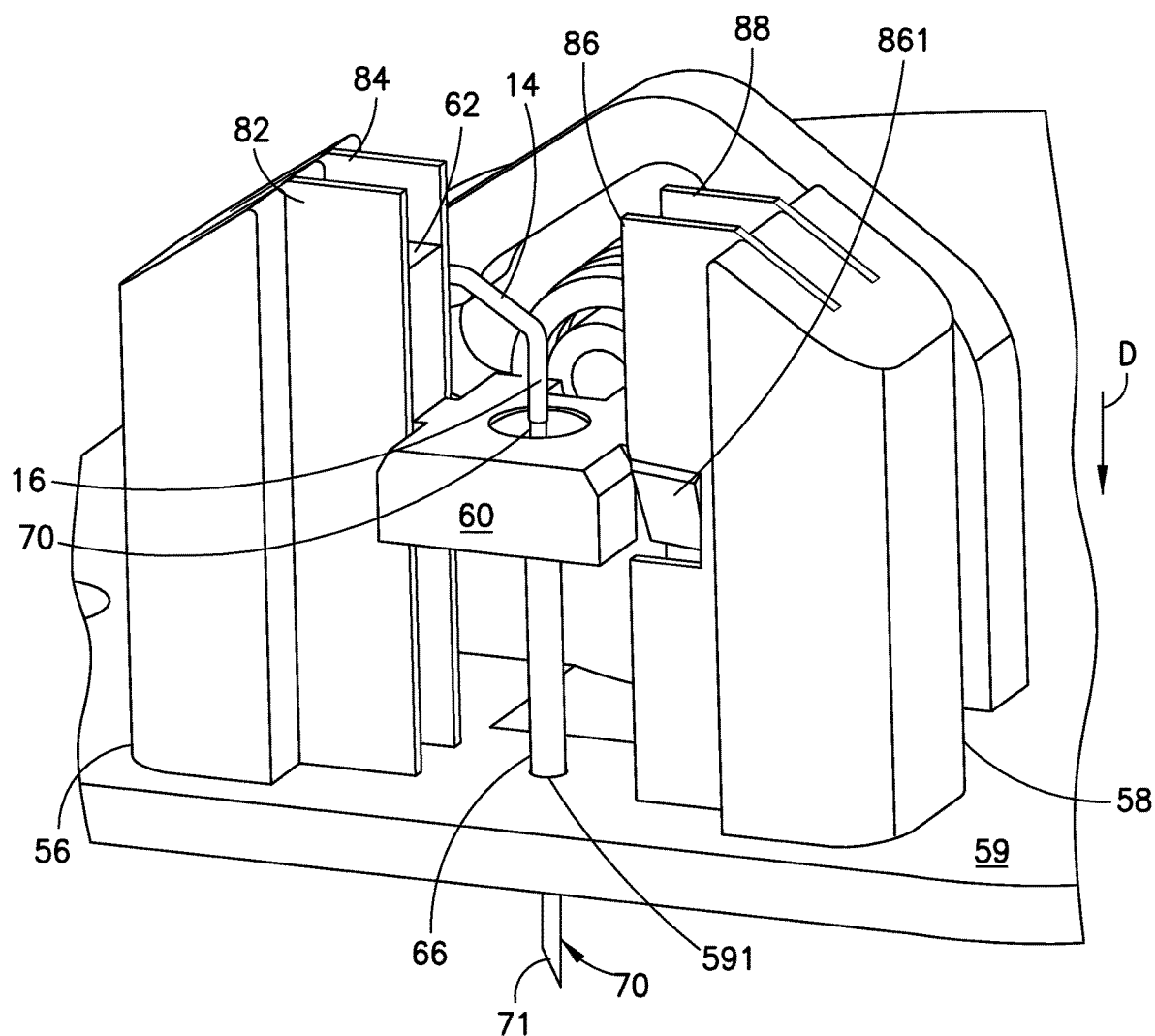
FIG. 10 is a perspective view of the insertion device of FIG. 9, illustrated without the needle carriage for clarity.
Figure 11:
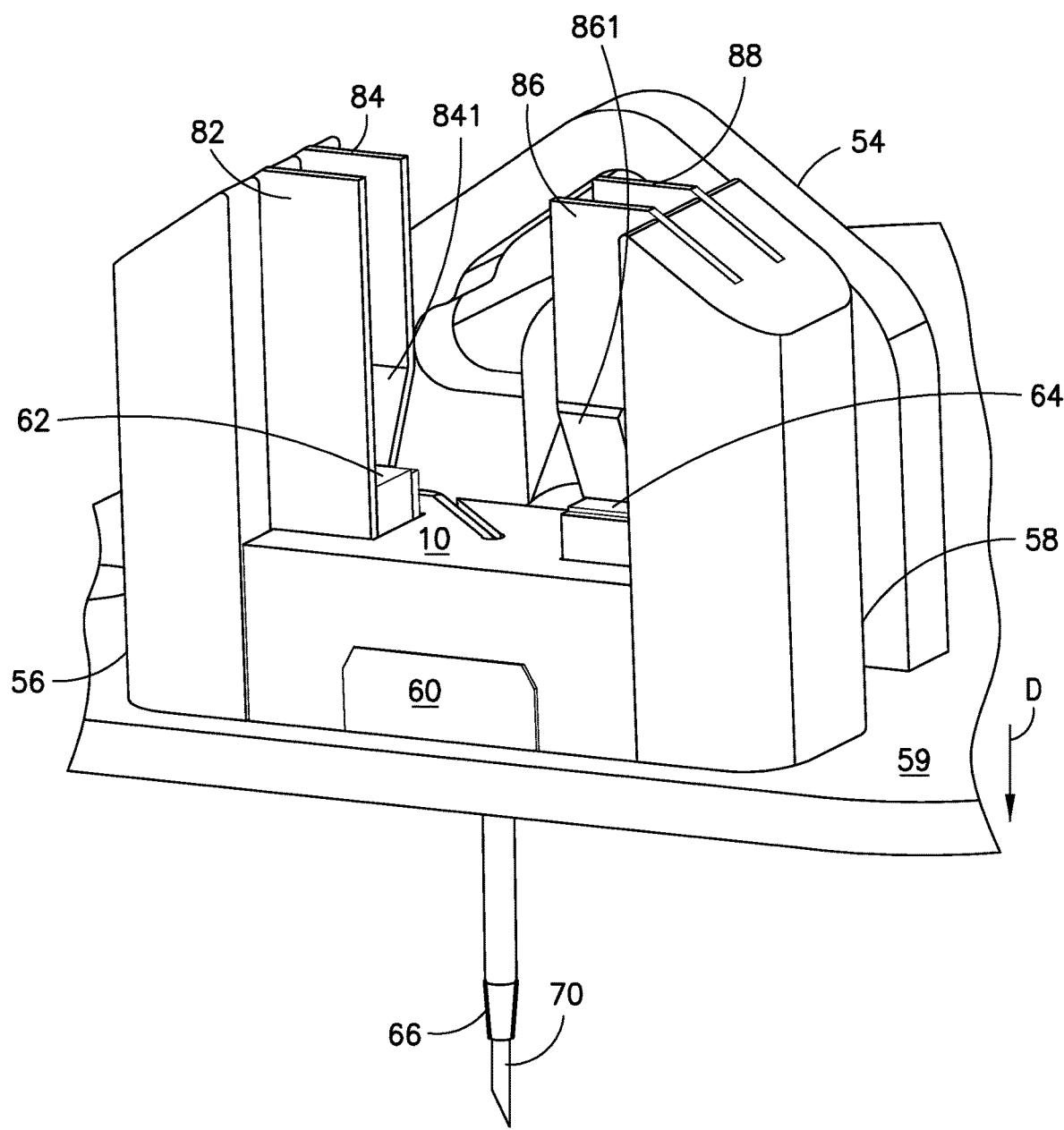
FIG. 11 is a perspective view of the insertion device of FIG. 10, illustrated with the needle carriage and the catheter carriage contacting the floor of the base and fully extending the introducer needle into the infusion site.

FIG. 10 is a perspective view of the cannula insertion device 7 of FIG. 9, similar to that of FIG. 9 but illustrated without the needle carriage 10 for clarity. In the position illustrated in FIG. 10, as the slides 62, 64 of the catheter carriage 60 slide downwardly between the rails 82, 84, 86, 88, the resilient tabs 841, 861 bend out of the way, permitting both the needle carriage 10 and the catheter carriage 60 to slide downward, along the rails 82, 84, 86, 88, without being hindered by the presence of the resilient tabs 841, 861, as illustrated in FIGS. 10 and 11. In addition, as illustrated in FIG. 10, the upper end of the introducer needle 70 is connected to a connector 16 of the flexible fluid line 14 and is in fluid communication with a reservoir and pump (not shown) so that the introducer needle 70 can deliver insulin to the infusion site. The introducer needle 70 is typically a hypodermic needle, a hollow metal tube with a sharp end 71 at an open end thereof.

FIG. 11 is a perspective view of the insertion device of FIG. 10, illustrated with the needle carriage 10 and the catheter carriage 60 resting on the base floor 59, with the introducer needle 70 and catheter 66 fully extending through the exit hole 591 (as illustrated in FIG. 10) of the base floor 59. In FIG. 11, the slides 62, 64 of the catheter carriage 60 are positioned below the resilient tabs 841, 861 of the rails 84, 86 and in this position, the resilient tabs 841, 861 have returned to their bent positions (as in FIG. 8) in which the resilient tabs 841, 861 extend or pivot toward opposing rails. This locks the catheter carriage 60 on the base 50 by preventing the slides 62, 64 of the catheter carriage 60 from sliding upward in the direction opposite to direction "D". FIG. 11 illustrates the introducer needle 70 positioned through the catheter 66, that is fully inserted into a user's skin (not shown), along with the catheter 66.

Figure 12:
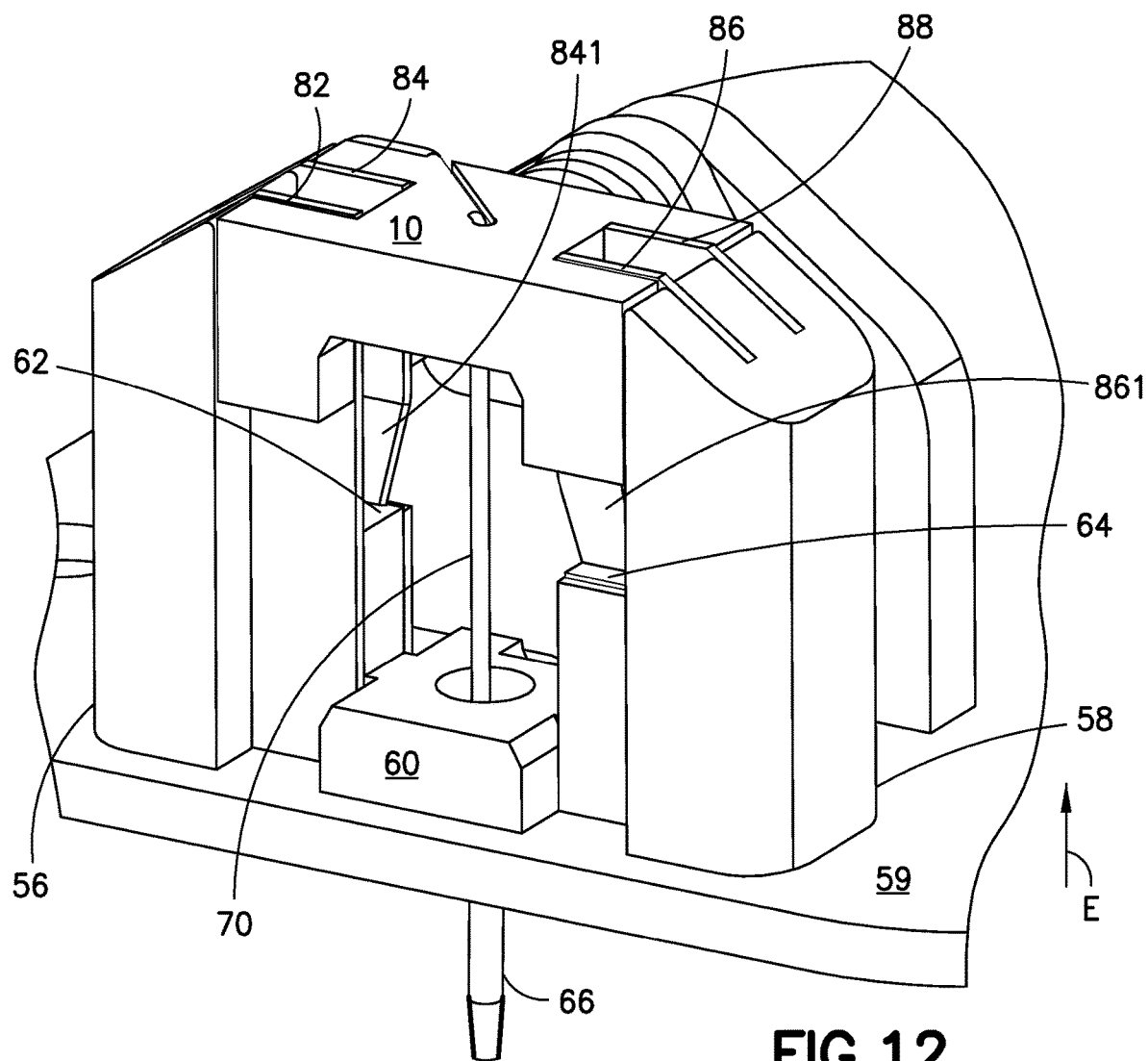
FIG. 12 is a perspective view of the insertion device of FIG. 11, illustrated with the needle carriage returning to its uppermost position to retract the introducer needle from the infusion site, while the catheter carriage remains locked at the floor of the base.
Figure 12A:
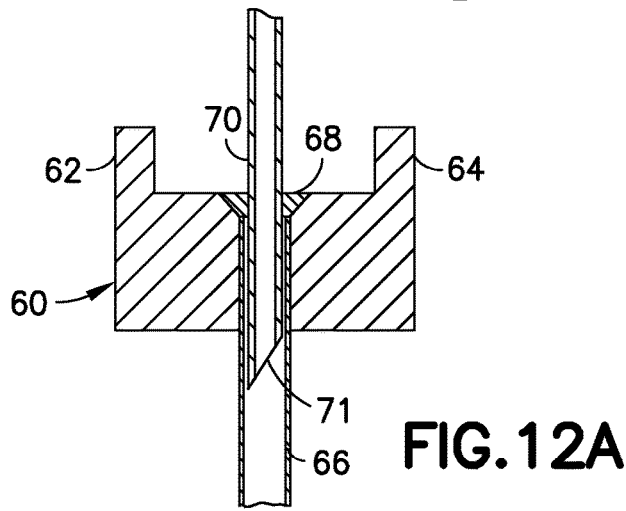
FIG. 12A is a cross-sectional view of the catheter carriage, introducer needle and septum of FIG. 12.

FIG. 12 is a perspective view of the cannula insertion device 7 of FIG. 11, illustrated with the needle carriage 10 returning to its uppermost position (as in FIG. 8) to retract the introducer needle 70 back through the exit hole 591 of the base floor 59, while the catheter carriage 60 remains locked at or near the base floor 59 of the base 50 by the resilient tabs 861, 841 swinging back or returning to their original form, which prevents the catheter carriage 60 from being retracted upward in the direction of "E". FIG. 12 illustrates the upward movement of the needle carriage 10, to extract the introducer needle 70 from the user's skin while the catheter 66 remains lodged into the user's skin. The needle carriage 10 stays locked at its uppermost position after the tension on the torsion spring 30 has been released. In FIG. 12, the sharp end 71 of the introducer needle 70 penetrates a septum (not shown). FIG. 12 A is a cross-sectional view of the catheter carriage 60, illustrating the sharp end 71 of the introducer needle 70 penetrating a septum 68, so that insulin pumped out of the sharp end 71 of the introducer needle 70, via the fluid line 14 and connector 16, is in fluid communication with the infusion site via the catheter 66 without leakage. The septum 68 prevents backflow of insulin via the catheter 66 from the infusion site.

One of the advantages of the cannula insertion device 7, illustrated in FIGS. 5-12, is that it can be smaller than existing devices, which can allow for a smaller overall patch pump. Another advantage of the cannula insertion device 7 is that the insertion of the introducer needle 70 can be perpendicular or substantially perpendicular to the surface of the user's skin, which allows a shorter insertion wound and a reduction in scar tissue in comparison with other devices that insert a cannula (metal cannula or plastic catheter) at an acute angle from the surface of the skin. Yet another advantage is that the insertion of both the introducer needle 70 and the catheter 66 into a user's skin and the retraction of the introducer needle 70 are accomplished by using a single spring device, which can reduce the overall number of parts, complexity and cost.

An important aspect when developing an insulin patch pump is its overall size. In other words, the smaller the footprint and the lower the profile of the patch pump, it is more likely that a user would be willing to wear it. Hence it is important to minimize the size of the patch pump. In order to do so, it is necessary to reduce one or more components of the path pump.

In an exemplary embodiment of the present application, by reducing the size of the cannula insertion device 7 as compared with other insertion devices, a patch pump that incorporates the cannula insertion device 7 can be reduced in its overall size and footprint. In the cannula insertion device 7, by advantageously capturing a greater range of rotation of the torsion spring 30, the linkage 20 and yoke 54 can be further reduced in size.

Figure 13:
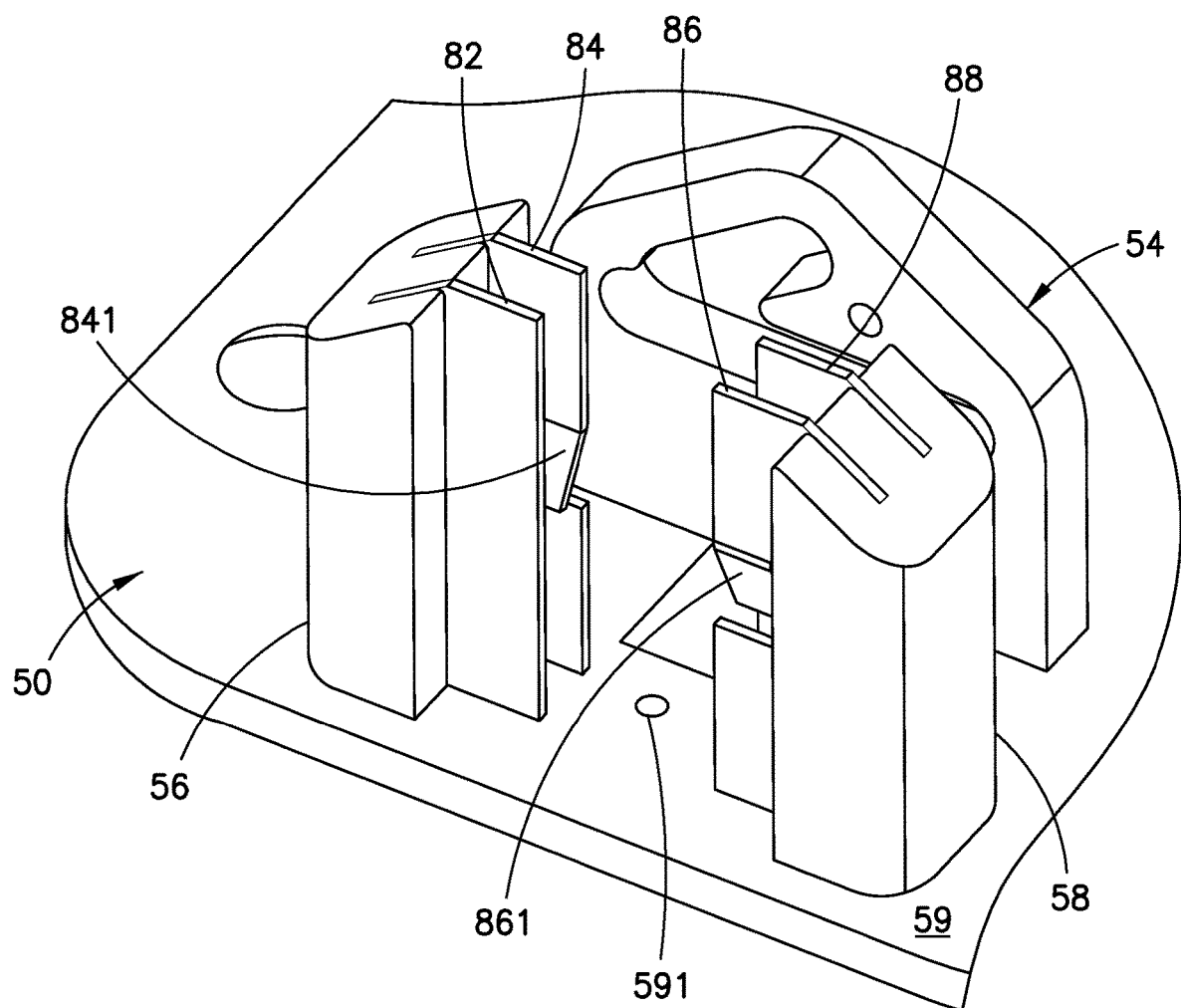
FIG. 13 is perspective view of a sub-assembly of some components of the insertion device of FIG. 5, illustrating the base, rails connected to base uprights, and a yoke.

FIGS. 13-18 illustrate a preferred sequence for assembling an exemplary embodiment of the cannula insertion device 7. FIG. 13 is perspective view of a sub-assembly of the cannula insertion device 7 of FIG. 5, illustrating a base floor 59 with a through-hole 591, rails 82, 84, 86, 88 connected to base uprights 56, 58, and a yoke 54. One or more of the components above can be made separately and assembled to form the base 50 or integrally molded together for ease of manufacture. In a preferred embodiment, the rails 84, 86 having resilient tabs 841, 861, preferably metallic in composition since the resilient tabs 841, 861 have to give way as the catheter carriage 60 slides between the rails, past the resilient tabs 841, 861 and then return to their original bent shapes after the catheter carriage 60 slides fully past the resilient tabs 841, 861. It is conceivable that even if one or more components were modified or eliminated, the cannula insertion device 7 would still be functional. For instance, a single base upright 56 can be used with its rails 82, 84.

However, in order to insure reliability, it is preferred that there are two opposing base uprights 56, 58 with their accompanying rails 82, 84, 86, 88. The yoke 54 is illustrated as being spaced apart from base uprights 56, 58, but it is conceivable that they are integrally formed together.

Figure 14:
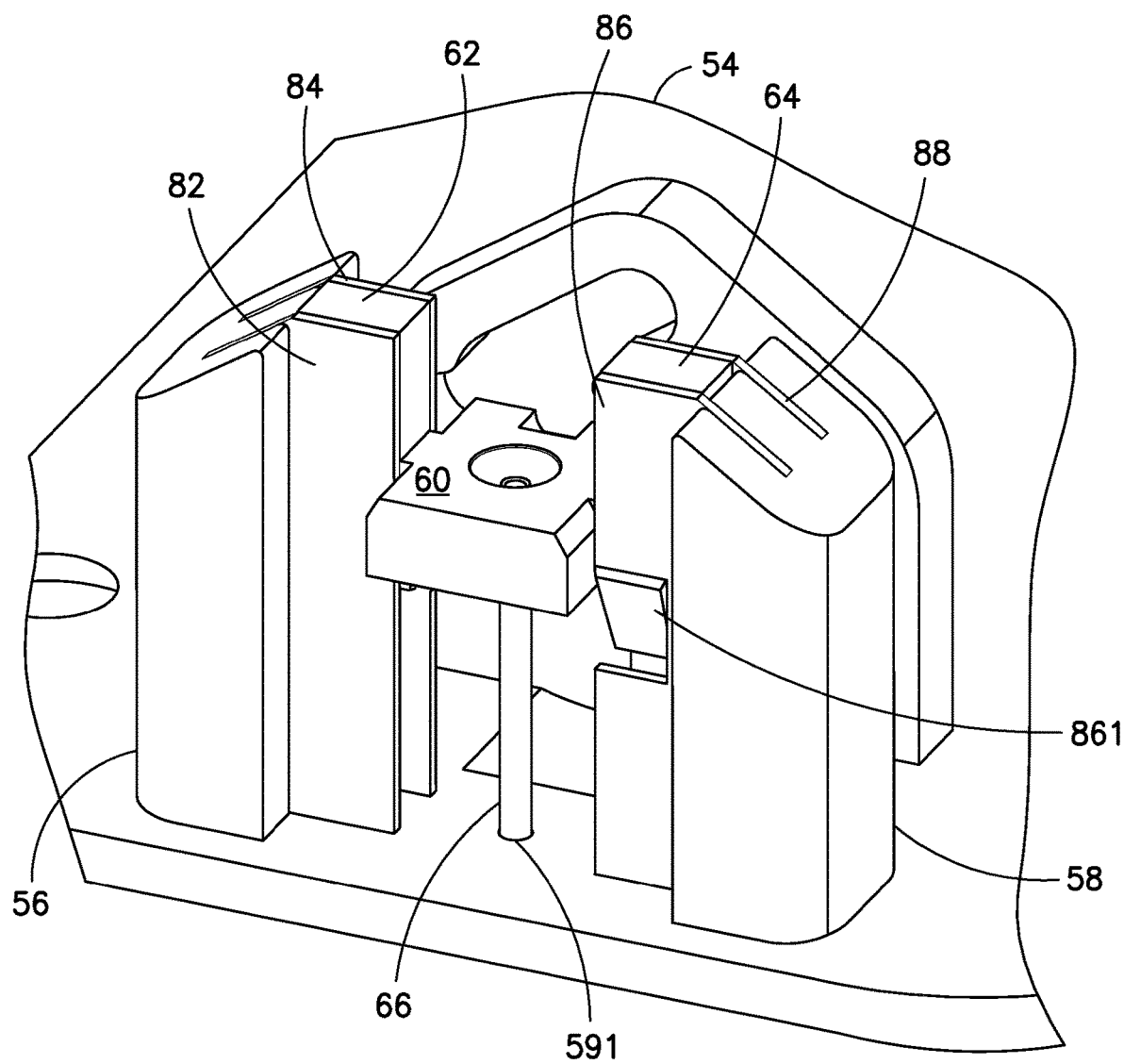
FIG. 14 is perspective view of the sub-assembly of FIG. 13, illustrated with the catheter carriage positioned in the rails.

FIG. 14 is perspective view of the sub-assembly of FIG. 13, illustrated with the first slide 62 of the catheter carriage 60 being positioned between the rails 82, 84 of the first base upright 56 and the second slide 64 of the catheter carriage 60 being positioned between the rails 86, 88 of the second base uprights 58. In FIG. 14, the catheter carriage 60 is at its highest position between the rails 82, 84, 86, 88. The catheter 66 is attached to the catheter carriage and is guided in or above the exit hole 591 of the base floor 59. In this position, the slides 62, 68 of the catheter carriage 60 are positioned above the resilient tabs 841 and 861 of the rails 84 and 86.

FIG. 15 is a perspective view of the sub-assembly of linkage 20 and the torsion spring 30 of the cannula insertion device 7 of FIG. 5. The spring 30 is illustrated as being assembled around the first post 22 of the linkage 20, with a bent leg 32 of the spring 20 being inserted into the hole 241 at one side of the main flanged portion 24 of the linkage 20, and the other end of the spring 30 being a straight leg 34. A through-hole 243 extends through the main flanged portion 24 of the linkage 20 for receiving the pin 90 (illustrated in FIGS. 19-21). The post 22 includes a hole 221 for receiving the axle post 12 of the needle carriage 10. A second post 26 extends outwardly from another side of the main flanged portion 24 and distant from the first post 22. A mandrel 28 having a larger diameter than the post 26 extends from the post 26.

Figure 16:
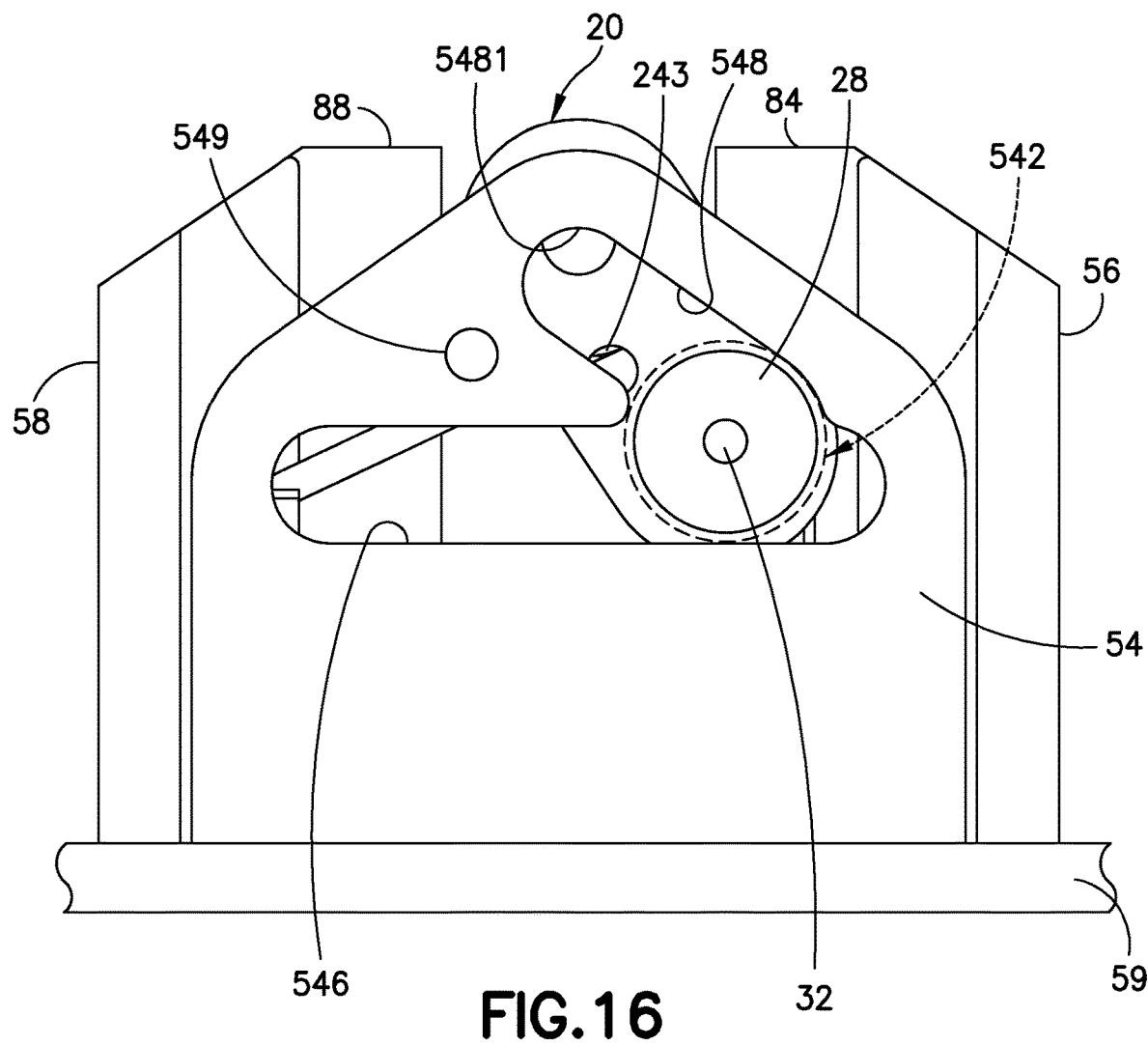
FIG. 16 is a front view of the device of FIG. 14, illustrated with a flanged part of the linkage being inserted into an opening of the yoke.

FIG. 16 is a front view of a sub-assembly of the cannula insertion device 7 of FIG. 14, illustrated with the mandrel 28 of the linkage 20 being inserted into a large opening 542 of the yoke 54, the large opening 542 having a diameter slightly larger than that of the mandrel 28 for receiving the mandrel 28 therethrough. The second post 26 of the linkage 20 is slidable into both the elongated slots 546,548 of the yoke 54, while the mandrel 28 is only slidable through the large opening 542.

Figure 17:
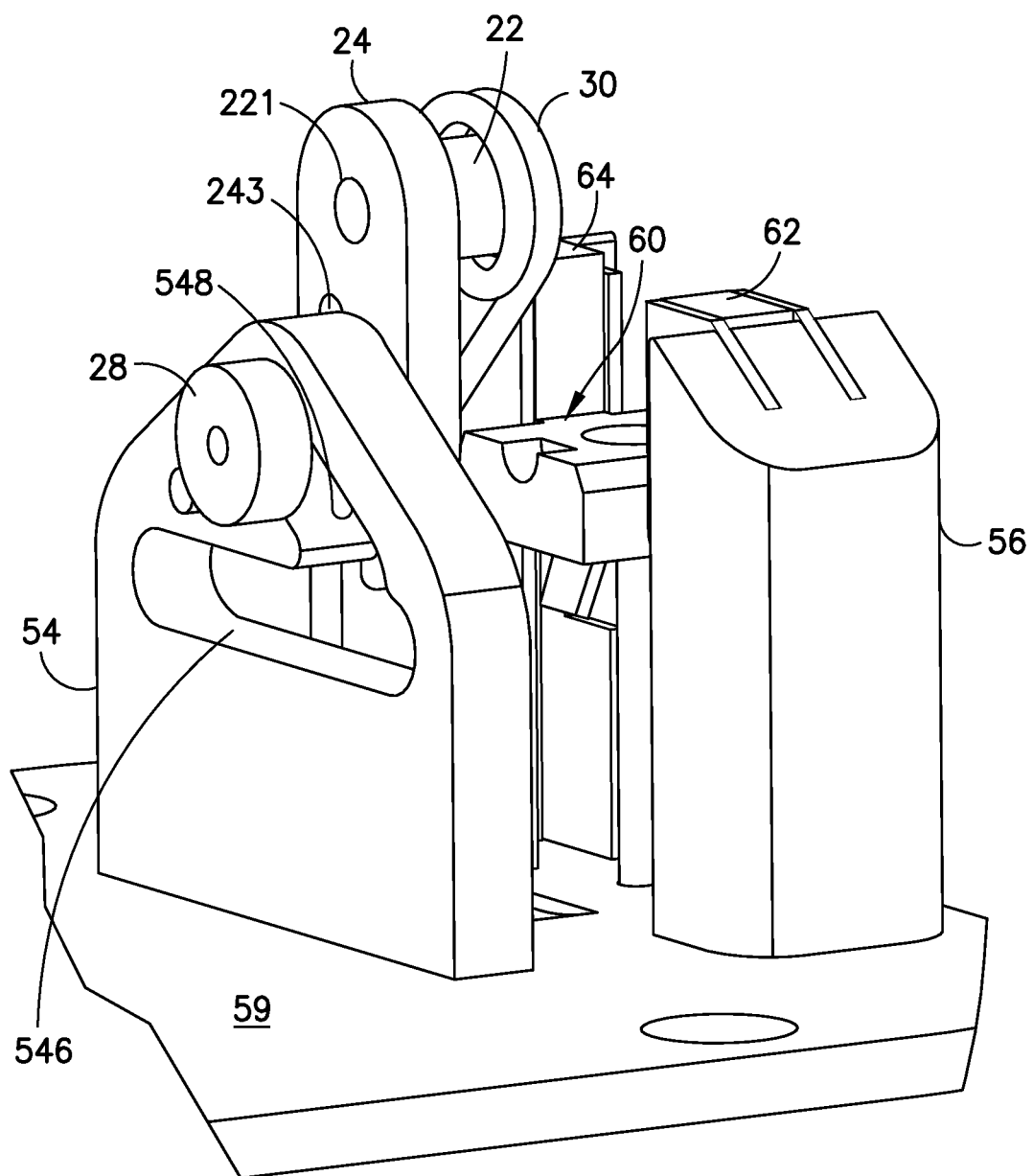
FIG. 17 is a perspective view of the inserter device of FIG. 16, illustrated with the flanged part of the linkage moved along a channel to its uppermost position.

FIG. 17 is a perspective view of a sub-assembly of the cannula insertion device 7 of FIG. 16, illustrated with the second post 26 moved along the second elongated slot 548 to the uppermost position thereof. Hence, the mandrel 28 of the linkage 20 is also positioned at its uppermost position. The catheter carriage 60 is illustrated in FIG. 17 with its slides 62, 64 at their uppermost positions between the rails 82, 84, 86, 88 of the base uprights 56, 58.

Figure 18:
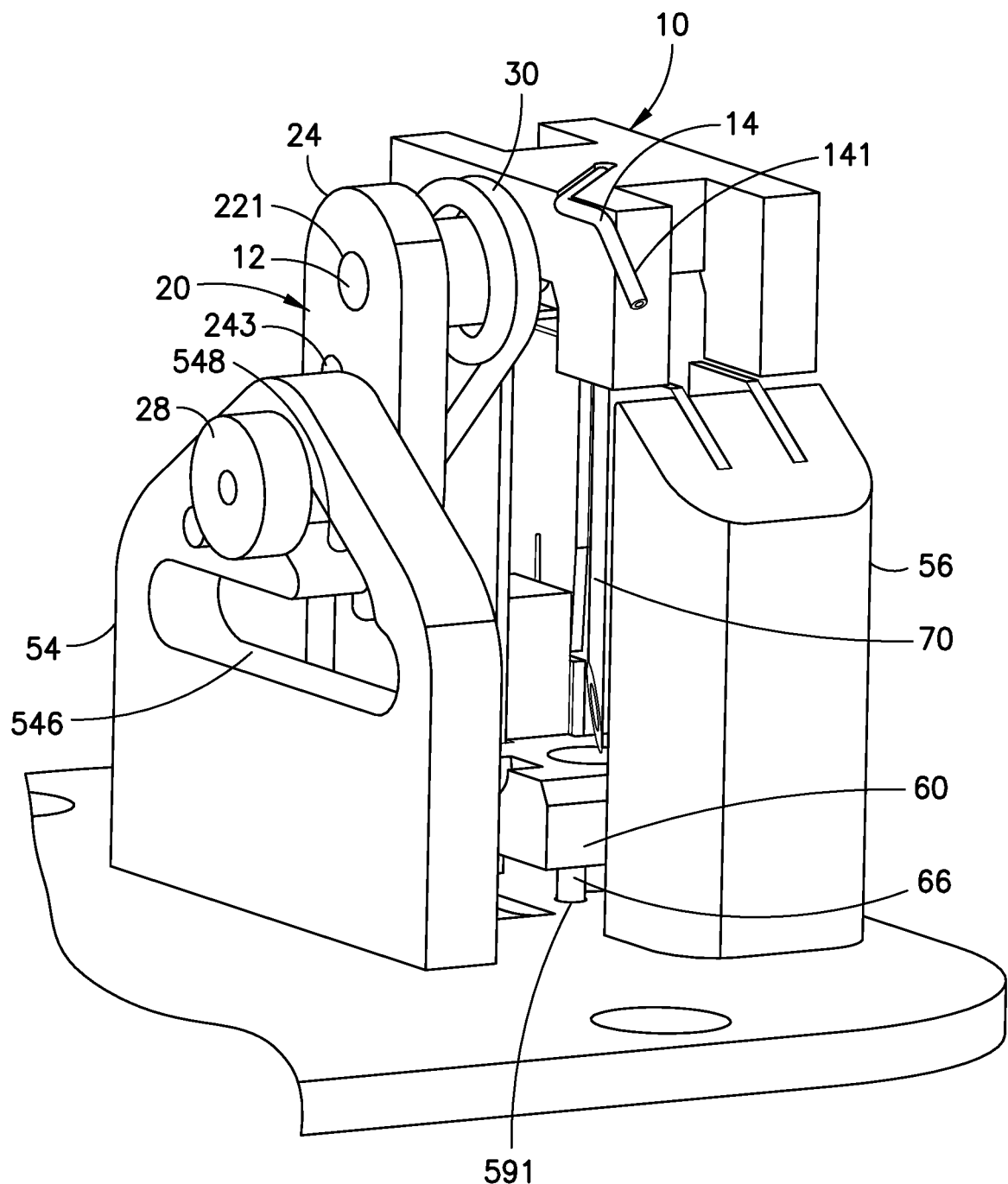
FIG. 18 is a perspective view of the inserter device of FIG. 17, illustrated with the needle carriage connected to the linkage and positioned above the catheter carriage.

FIG. 18 is a perspective view of a sub-assembly of the cannula insertion device 7 of FIG. 17, illustrated with the axle post 12 of the needle carriage 10 received in the hole 221 of the linkage 20, the introducer needle 70 of the needle carriage 10 positioned above the catheter 66 of the catheter carriage 60 that has been slid downwards along the rails 82, 84, 86, 88.

Figure 19:
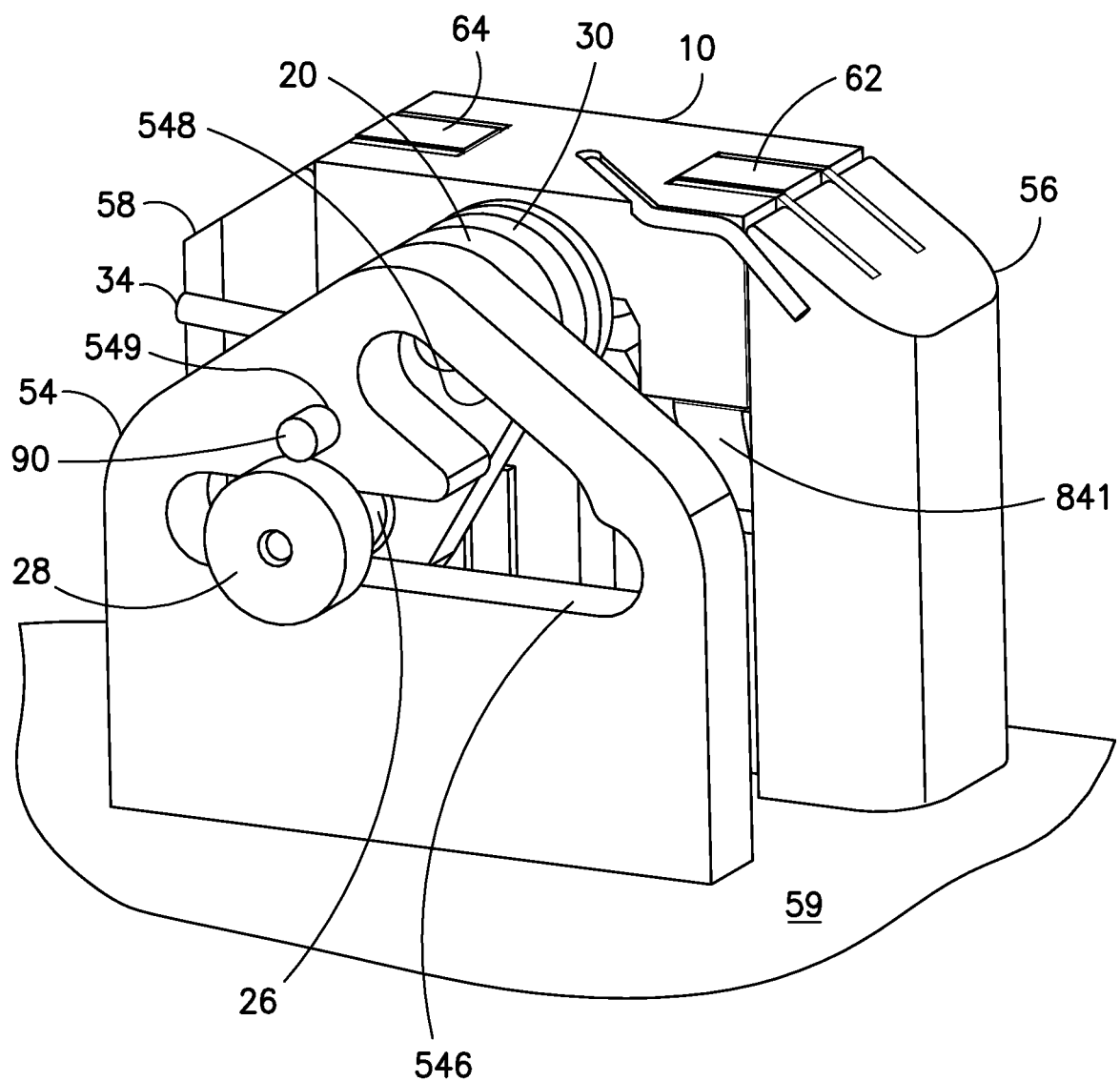
FIG. 19 is a perspective view of the inserter device of FIG. 18, illustrated with the needle carriage and the catheter carriage at their uppermost positions on the rails and a pin locking the linkage to the yoke.
Figure 19A:
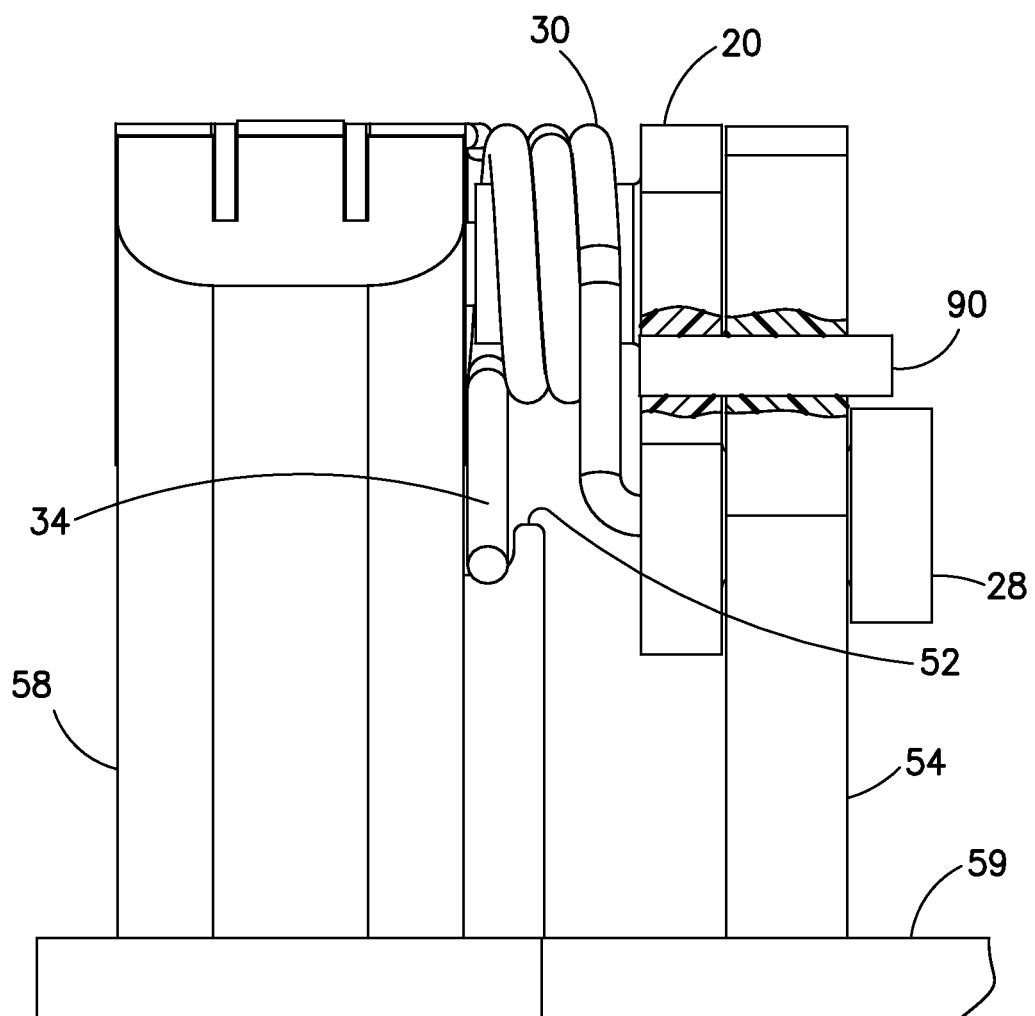
FIG. 19A is a partial cutout view of the inserter device of FIG. 19, illustrated with the needle 90 inserted into the yoke and linkage.

FIG. 19 is a perspective view of a sub-assembly of the cannula insertion device 7 of FIG. 18. The needle carriage 10 is slid onto the rails 82, 84, 86, 88, which pushes the second post 26 downwards along the second elongated slot 548, past the large opening 542 and into the first elongated slot 546 until hole 243 of the linkage and hole 549 of the yoke 54 align. The pin 90 is then placed into the aligned holes 243, 549 to lock the linkage 20 to the other components of the cannula insertion device 7. At this position, the slides 62, 64 of the catheter carriage 60 can be slid upwardly in the rails 82, 84, 86, 88 and positioned above the locking or resilient tabs 841, 861 of the rails 84 and 86. FIG. 19A is a partial cutout view that illustrates with the needle 90 that is inserted into the yoke and linkage to lock the tensioned spring 30, prior to activation.

Figure 20:
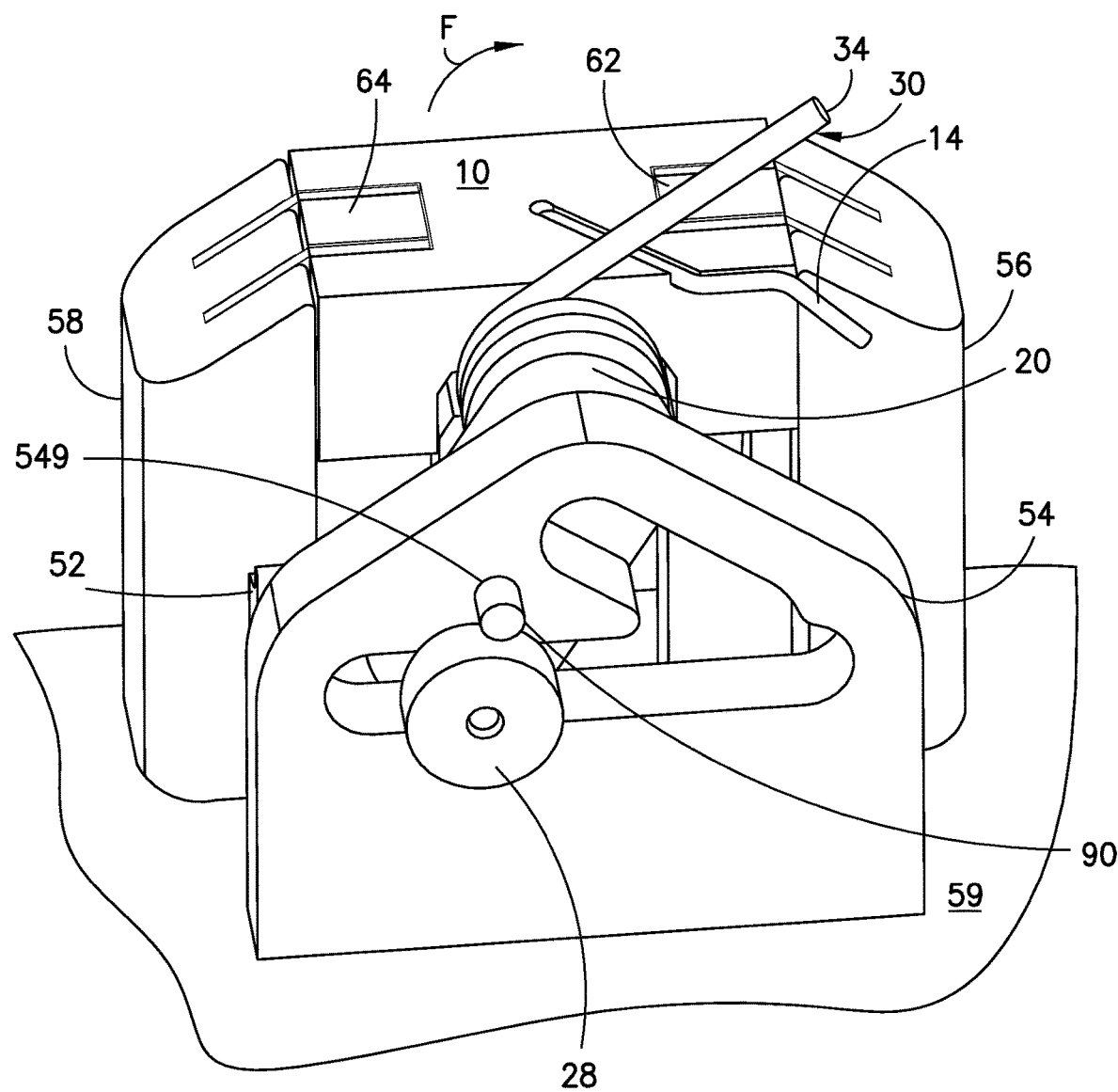
FIG. 20 is a perspective view of the inserter device of FIG. 20, illustrating how the torsion spring is rotated to become tensioned.

FIG. 20 is a perspective view of the cannula insertion device 7 of FIG. 20, illustrated with the free leg 34 of the torsion spring 30 being rotated around the axle post 12 of the needle carriage 10, shown in the clockwise direction "F" to tension the torsion spring 30 to store potential energy.

Figure 21:
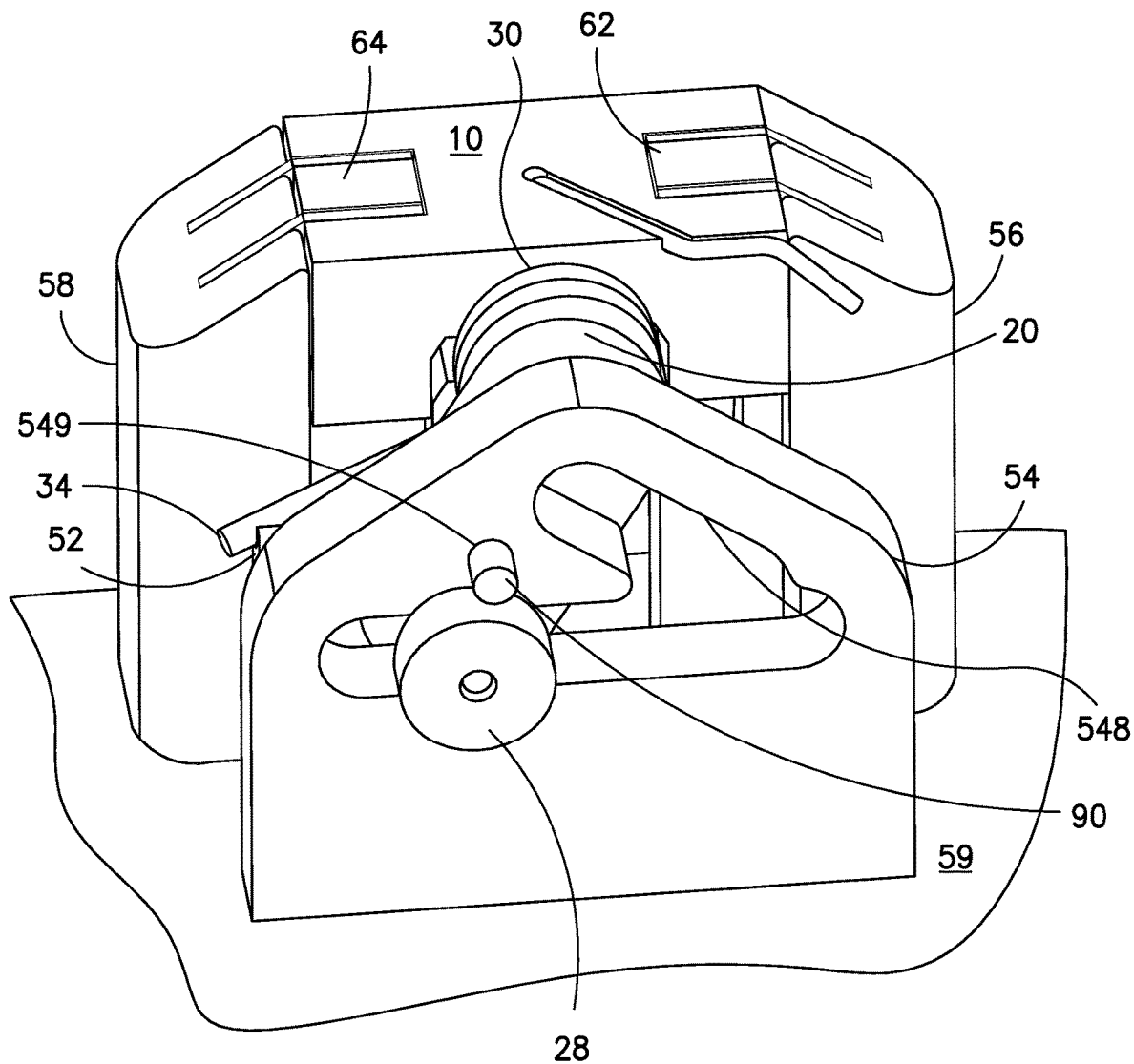
FIG. 21 is a perspective view of the inserter device of FIG. 19, illustrated with the open end of the torsion spring abutting a notch on the base and the inserter device positioned for activation.

FIG. 21 is a perspective view of the cannula insertion device 7 of FIG. 19, illustrated with the straight leg 34 of the tensioned torsion spring 30 abutting against a notch 52 on the second base upright 58 and the cannula insertion device 7 is now prepared or loaded for activation. When the user activates a release button (not shown) on the patch pump 1, 1A, the pin 90 is pulled out of the hole 243 of the linkage 20, which causes the release of the tensioned torsion spring 30, causing the stored potential energy in the tensioned torsion spring 30 to be translated into linear motions of the needle carriage 10 and catheter carriage 60, via the Scotch-yoke mechanism, as described above. Preferably, the pin 90 is in mechanical connection with the release button on the patch pump 1, 1A such that upon actuation of the release button by a user, the pin 90 is retracted from the linkage 20, to release the tension on the torsion spring 30 to activate the cannula insertion device 7 and thereby insert the introducer needle 70 and catheter 66 into the insertion site and then retract only the introducer needle 70, as described above. Alternatively, an electrical actuator can be used to withdraw the pin 90 from the linkage 20 in response to the user's operation of an electrical switch, electrical push button or other type of electrical input device located on the body of the patch pump 1, 1A or on a remote control device.

Alternative or variations on the described cannula insertion device 7 are possible. For instance, the device could be locked and released by an obstruction under the needle carriage 10 or catheter carriage 60 instead of the pull pin 90. In addition, it is envisioned that there can be other alternatives to the pull pin 90, which acts as a locking device as the torsion spring 30 is wound, and as an activation device when the pull pin 90 is then removed. For instance, the locking device and the activation device can be separate units.

As used in this description, the terms "front", "rear", "upper", "lower", "upwardly", "downwardly", and other orientational descriptors are intended to facilitate the description of the exemplary embodiments of the present invention, and are intended to limit the structure of the exemplary embodiments of the present invention to any particular position or orientation.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:
1. A patch pump comprising:
   a reservoir;
   a pump;
   a cannula insertion device comprising a yoke having a first channel and a second channel, a carriage carrying a catheter, and a linkage linking the yoke to the carriage, the cannula insertion device powered by a torsion spring for inserting an introducer needle and the catheter into an infusion site and for retracting the introducer needle while the catheter remains inserted into the infusion site;

wherein the first channel and the second channel comprise an enlarged opening where the first channel and the second channel overlap;

wherein infusate from the reservoir is pumped by the pump into the infusion site after the catheter is inserted into the infusion site.

2. The patch pump as claimed in claim 1, wherein the introducer needle and catheter are inserted substantially perpendicular to the infusion site.

3. The patch pump as claimed in claim 1, further comprising a switch for actuating the insertion of the catheter into the infusion site.

4. The patch pump as claimed in claim 1, further comprising a metering system for metering the amount of infusate pumped from the reservoir by the pump.

5. The patch pump as claimed in claim 4, further comprising a controller for controlling the delivery of selected doses of infusate into the infusion site.

6. The patch pump as claimed in claim 1, further comprising a power source for powering at least one of the pump, metering system and controller.

7. The patch pump as claimed in claim 1, further comprising a cover for housing the cannula insertion device, reservoir, pump, metering system and controller.

8. The patch pump as claimed in claim 1, further comprising an exit aperture through which the introducer needle and the catheter are inserted into the infusion site and through which the introducer needle is retracted after the catheter is inserted into the infusion site.

\* \* \* \* \*